US012629457B2

(12) United States Patent   (10) Patent No.: US 12,629,457 B2
Riman et al.                     (45) Date of Patent:     May 19, 2026

(54) STRUCTURAL IMPLANT FOR BONE REPAIR

(71) Applicant: Rutgers, The State University of New Jersey, New Brunswick, NJ (US)

(72) Inventors: Richard E. Riman, Piscataway, NJ (US); Berra Beyoglu Siglam, Monroe Township, NJ (US); Joachim B. Kohn, Piscataway, NJ (US); Yong Mao, Basking Ridge, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 874 days.

(21) Appl. No.: 17/817,941

(22) Filed: Aug. 5, 2022

(65) Prior Publication Data

US 2023/0065455 A1     Mar. 2, 2023

Related U.S. Application Data

(60) Provisional application No. 63/229,706, filed on Aug. 5, 2021.

(51) Int. Cl.
*A61L 27/56*      (2006.01)
*A61L 27/02*      (2006.01)
(Continued)

(52) U.S. Cl.
CPC ............. *A61L 27/56* (2013.01); *A61L 27/025* (2013.01); *A61L 27/34* (2013.01); *C04B 35/22* (2013.01);
(Continued)

(58) Field of Classification Search
CPC ......... C04B 35/22; A61L 27/025; A61L 27/56
See application file for complete search history.

(56) References Cited

U.S. PATENT DOCUMENTS

| | | |
|---|---|---|
| 5,981,412 A | 11/1999 | Hench et al. |
| 2001/0018614 A1 | 8/2001 | Bianchi |

(Continued)

FOREIGN PATENT DOCUMENTS

| | | | |
|---|---|---|---|
| CA | 1122779 A | * | 5/1982 |
| JP | S52135899 A | * | 11/1977 |

(Continued)

OTHER PUBLICATIONS

De Almeida et al. Calcium silicate as a graft material for bone fractures: a systematic review. Journal of International Medicine Research. Bol. 46. May 30, 2018. pp. 2537-2548 (Year: 2018).*

*Primary Examiner* — Cachet I Proctor
(74) *Attorney, Agent, or Firm* — FOX ROTHSCHILD LLP

(57) ABSTRACT

Disclosed are composite materials comprising a porous, carbonated, calcium silicate ceramic having a microstructure comprising interconnected open pores; where the calcium silicate surface defining the pores is partially or completely coated with an amorphous silica layer, and the silica coating comprises an overlayer of calcium carbonate crystals; where the silica coating and calcium carbonate overlayer form a network that interconnects throughout the ceramic microstructure, but do not completely occlude the pores. Also disclosed are methods of forming such composite materials.

19 Claims, 8 Drawing Sheets

(51) Int. Cl.

| | | |
|---|---|---|
| *A61L 27/34* | (2006.01) | |
| *C04B 35/22* | (2006.01) | |
| *C04B 35/645* | (2006.01) | |
| *C04B 38/00* | (2006.01) | |

(52) U.S. Cl.

CPC ........ *C04B 35/645* (2013.01); *C04B 38/0054* (2013.01); *C04B 38/0096* (2013.01); *A61L 2430/02* (2013.01); *C04B 2235/3454* (2013.01); *C04B 2235/656* (2013.01)

(56) References Cited

U.S. PATENT DOCUMENTS

2004/0009598 A1    1/2004    Hench et al.

| | | | | |
|---|---|---|---|---|
| 2012/0312194 | A1* | 12/2012 | Riman | .................... C04B 28/10 106/796 |
| 2013/0063898 | A1* | 3/2013 | Schuett | ................... H01L 23/42 219/85.15 |
| 2014/0127450 | A1* | 5/2014 | Riman | ................. C04B 35/622 428/105 |
| 2014/0127458 | A1* | 5/2014 | Zambrzycki | .......... C04B 28/188 428/141 |
| 2014/0272216 | A1* | 9/2014 | Deo | ........................ C04B 38/02 428/221 |
| 2015/0266778 | A1* | 9/2015 | Riman | ................. B28B 11/245 106/286.6 |

FOREIGN PATENT DOCUMENTS

| | | | | |
|---|---|---|---|---|
| JP | H06263510 A | * | 9/1994 | .......... C04B 28/188 |
| WO | 2002004606 A1 | | 1/2002 | |

* cited by examiner

STRUCTURAL IMPLANT FOR BONE REPAIR

CROSS REFERENCE TO RELATED APPLICATION

The present application claims priority benefit under 35 U.S.C. § 119(e) of U.S. Patent Application Ser. No. 63/229,706 filed Aug. 5, 2021, the disclosure of which is incorporated by reference.

FIELD OF THE INVENTION

The invention is related to the preparation and use of ceramic and/or composite materials having the features required for use as bone implants, including biocompatibility, osteoinductivity (osteogenicity) and mechanical compatibility with human cortical bone.

BACKGROUND

Given the general increase in human lifespan, there is a growing need for bioactive bone implant material to repair bone defects caused by injury, infection or tumor, and to speed the healing process. Much research been conducted to find suitable bioactive materials for the repair of these bone defects. In the development of new biomaterials for bone replacement, the biochemical and biomechanical compatibility of implant material with host bone are essential parameters to consider. Moreover, implant materials that provide not only structural support (osteoconductivity) but also activate bone regeneration by stimulating osteoblastic cell proliferation and osteogenic differentiation of human mesenchymal stem cells (hMSC) (osteoinduction) are ideal for the repair of such bone defects. 45S5 bioglass is a well-studied bioactive glass composition having both osteoinductivity and osteoconductivity; however, the bioglass has poor mechanical properties, specifically high brittleness, low strength and low fracture toughness. Thus, it cannot be used for load-bearing implant applications. As such, there remains a need for ceramic composites that are mechanically and biologically compatible with human cortical bone, and which also possess osteoinductivity in order to promote bone growth and healing processes.

SUMMARY OF THE DISCLOSURE

The present invention provides such ceramic composites and methods to meet these needs.

The ceramic composites disclosed herein meet the requirements for biomechanical compatibility, biocompatibility and osteoinductivity and are also useful for load-bearing bone implant applications.

As such, one object of the present invention is to produce calcium silicate-based ceramic composites that are mechanically and biologically compatible with human cortical bone and have osteoinductivity comparable to 45S5 bioglass that will promote bone growth and healing. To meet this objective, it has now been discovered that Low Temperature Solidification (LTS, carbonation) increases the density of High Temperature Sintering (HTS) processed calcium silicate scaffolds, thereby enhancing mechanical properties of the calcium silicate scaffolds, and controlling the concentration of Ca and Si ions released from HTS calcium silicate ceramic to a range that promotes biocompatibility and osteoinductivity. The effect of combining HTS and LTS processes on the microstructure, mechanical properties, dissolution behavior, ion release profile, in vitro biocompatibility, and osteoinductivity of calcium silicate scaffolds was investigated. Processing calcium silicate compacts by the combination of HTS and LTS methods produced $CaSiO_3$—$CaCO_3$—$SiO_2$ composites. XRD patterns indicated development of $CaCO_3$ phases after the carbonation process. An increase in relative density up to 16% accompanied by a decrease in porosity, pore size was achieved, proportional to the degree of carbonation.

It was observed that the carbonation reaction products partially filled the pores of calcium silicate, effectively densifying the scaffolds. In at least one embodiment, a maximum compression strength of 279 MPa and bending strength of 65.5 MPa and fracture toughness of 1.87 $MPa \cdot m^{1/2}$ were achieved with the sintered, hydrothermally carbonated samples. The enhanced relative density, strength and toughness produced by carbonation of both green bodies (term of art used for previously shaped compressed ceramic particulate porous matrices or preforms, which are not sintered at high temperature) and sintered calcium silicate scaffolds was observed to improve mechanical compatibility with natural bone, increasing their potential as bone replacement materials.

The dissolution behavior of processed calcium silicate scaffolds was evaluated by immersion in Simulated Body Fluid (SBF). Soluble factor concentrations were found to decrease with increasing degree of carbonation. Thus, the drawbacks of rapid dissolution of sintered calcium silicate, with concomitant release of high concentrations of ions, could be addressed by adjusting the degree of carbonation thereby slowing and lowering the release of soluble ions.

In vitro cell proliferation and osteogenic differentiation tests were performed to evaluate biocompatibility and osteoinductivity (osteoinductive potential) of the processed calcium silicate scaffolds, respectively. In vitro cell experiments showed that calcium silicate composites produced by carbonation of sintered calcium silicate possessed significantly greater proliferation and significantly greater osteogenic differentiation (p<0.05) compared to only sintered $CaSiO_3$ or osteoinductive 45S5 bioglass. The inventive $CaSiO_3$—$CaCO_3$—$SiO_2$ composites produced by processing $CaSiO_3$ ceramics via combined HTS and LTS methods meet the requirements for repair of bone defects and constitute potential candidates for osteoinductive bone implant material.

One aspect of the invention is directed to a composite material comprising a porous, carbonated, calcium silicate ceramic having a microstructure comprising interconnected open pores; where the calcium silicate surface defining the pores is partially or completely coated with an amorphous silica layer, and the silica coating comprises an overlayer of calcium carbonate crystals; where the silica coating and the calcium carbonate overlayer form a network that interconnects throughout the ceramic microstructure, but do not completely occlude the pores.

Another aspect of the invention is directed to a composite material as above, produced by i) providing a $CaSiO_3$ ceramic compact having a microstructure comprising interconnected open pores around ceramic grain boundaries; and ii) subjecting the compact to hydrothermal carbonation under Low Temperature Solidification (LTS) conditions comprising heating in about 10 to about 30 psig $CO_2$ gas at <100° C., until the relative density increases by about 16% to about 20%. In some embodiments the $CaSiO_3$ ceramic compact is sintered at a temperature between about 1100° C. and about 1200° C. and cooled before subjecting to LTS conditions. In other embodiments the $CaSiO_3$ ceramic compact is sintered at about 1150° C.

The LTS conditions comprise heating at a temperature of about 50° C. to <100° C. in about 15 to about 25 psig $CO_2$ gas. In some embodiments the LTS conditions comprise heating at about 90° C. in about 20 psig $CO_2$ gas.

The above composite material can be in the form of a scaffold for implantation in vivo. The composite material can have an amorphous silica layer that comprises a calcium gradient. The compact of the composite material can be have a shape with dimensions to fit a bone defect prior to or after sintering.

A further aspect of the invention is directed to a method of forming a composite material, comprising the steps of: 1) providing a compact of a $CaSiO_3$ ceramic material having a microstructure comprising interconnected open pores; and 2) subjecting the compact to hydrothermal carbonation under Low Temperature Solidification (LTS) conditions comprising heating at <100° in about 10 to about 30 psig $CO_2$ gas C, until the relative density value increases by about 16% to about 20% to produce a carbonated ceramic material. In some embodiments the $CaSiO_3$ ceramic compact is sintered at a temperature between about 1100° C. and about 1200° C. and cooled before subjecting to LTS conditions. In some embodiments the $CaSiO_3$ ceramic compact is sintered at about 1150° C.

In the method as described above, the interconnected pores can have an average pore size between about 0.5 μm and about 3 μm. The LTS conditions of the method comprise heating at a temperature of about 50° C. to <100° C. in about 15 to about 25 psig of $CO_2$ gas. Preferably, the LTS conditions of the method comprise heating at a temperature of about 90° C. in about 20 psig of $CO_2$ gas.

The composite material formed by the above method preferably has a shape with dimensions to fit a bone defect prior to or after sintering.

Yet another aspect of the invention is directed to a method of repairing a bone defect caused by trauma, infection or removal of a tumor, where the method comprises filling the bone defect with the composite material described above.

Thus, in accordance with exemplary embodiments of the present invention, ceramic composite materials, and methods of making said ceramic composites result a wide range of desirable properties that may be optimized, including but not limited to biocompatibility, osteoinductivity and biocompatible mechanical properties as a result of the core/first layer/second layer structure of the ceramic composite.

It is to be understood that both the foregoing general description and the following detailed description are exemplary and explanatory only, and are not restrictive of the invention as disclosed.

DETAILED DESCRIPTION

Figure 1:
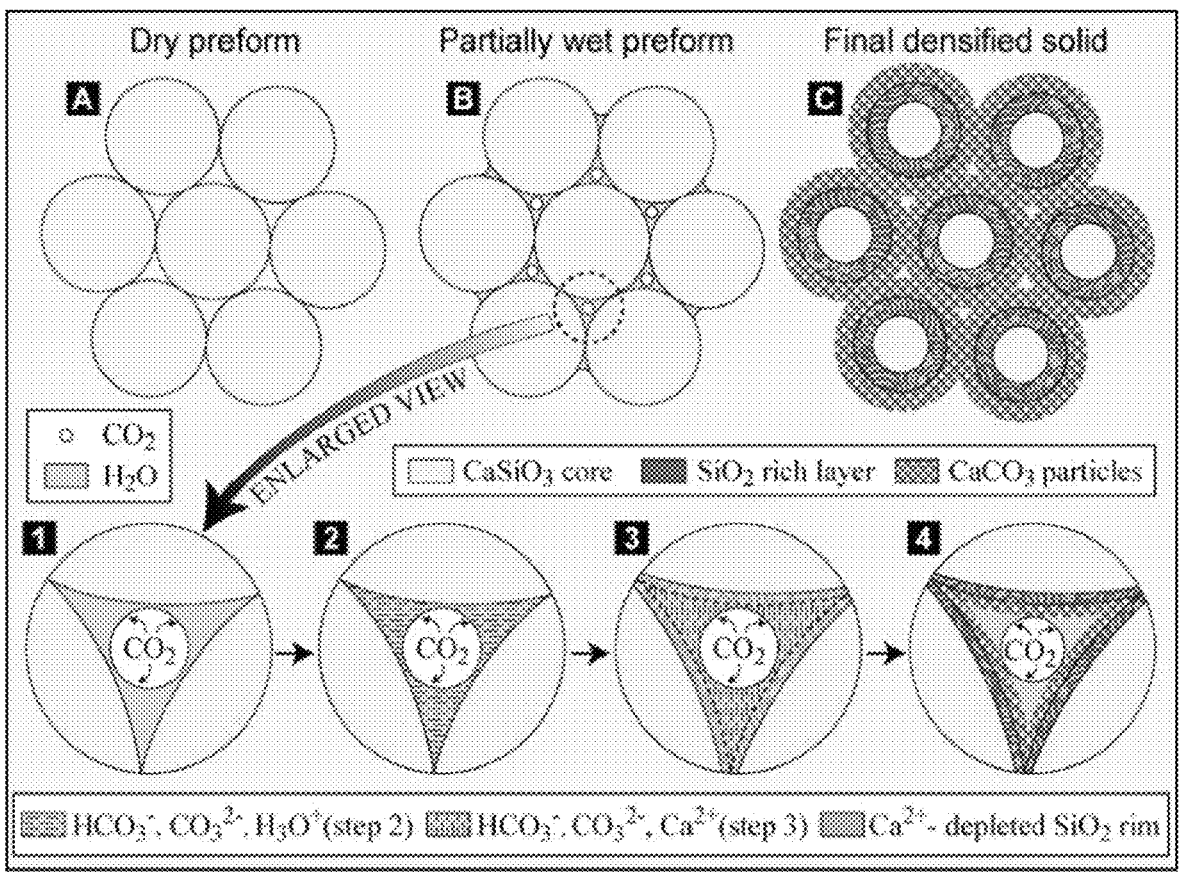
FIG. 1 shows a schematic diagram of the LTS process. (A) Dried porous $CaSiO_3$ preform; (B) Partially wet $CaSiO_3$ preform; (C) Final densified monolithic solid. Steps 1 to 4 represent the carbonation-densification process occurring in an individual pore: Step (1) Partially wet pore with $CO_2$; Step (2) Diffusion, dissolution and dissociation of $CO_2$; Step (3) Dissolution of $CaSiO_3$ by hydrogen ions; Step (4) Precipitation of solids. After the completion of step 4, the process takes place continuously following steps 2-4 until various kinetic factors slow down the process (e.g., thick $SiO_2$ reaction layers).
Figures 2A, 2B, 2C:
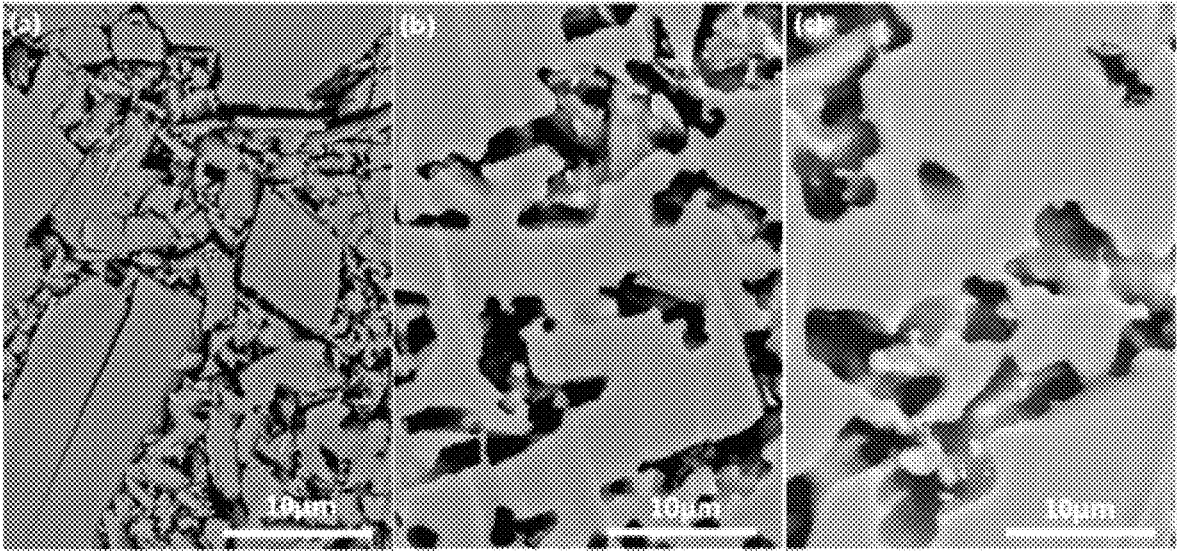
FIGS. 2A-2C show BSE images of Ion Beam Milled (IBM) surfaces of (2A) HTS1100, (2B) HTS1150, and (2C) HTS1200 samples.
Figures 3A, 3B, 3C, 3D:
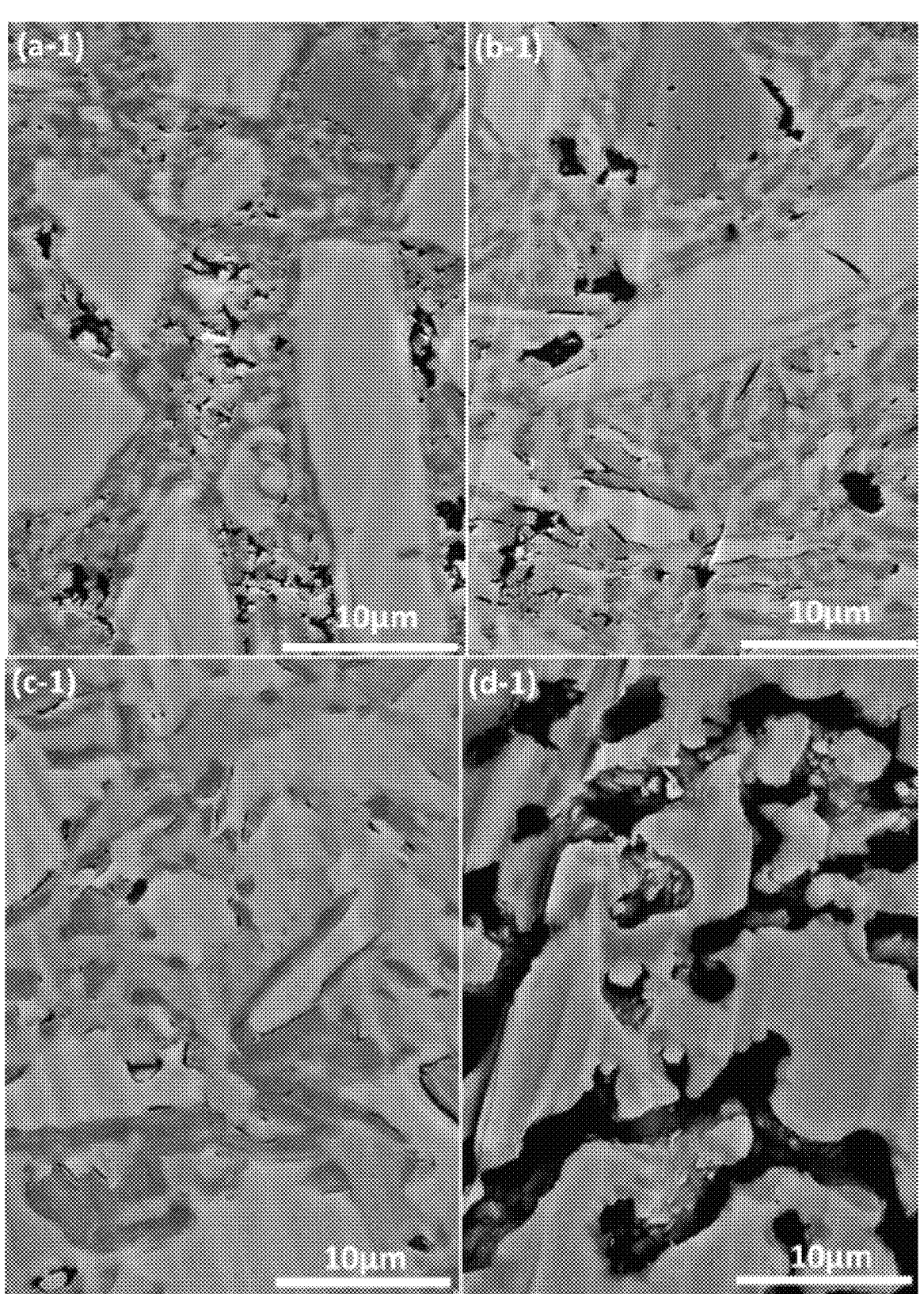
FIGS. 3A-3D show BSE images of Ion Beam Milled (IBM) surfaces of (3A) LTS, (3B) H1100LTS, (3C) H1150LTS and (3D) H1200LTS samples.
Figures 4A, 4B, 4C, 4D:
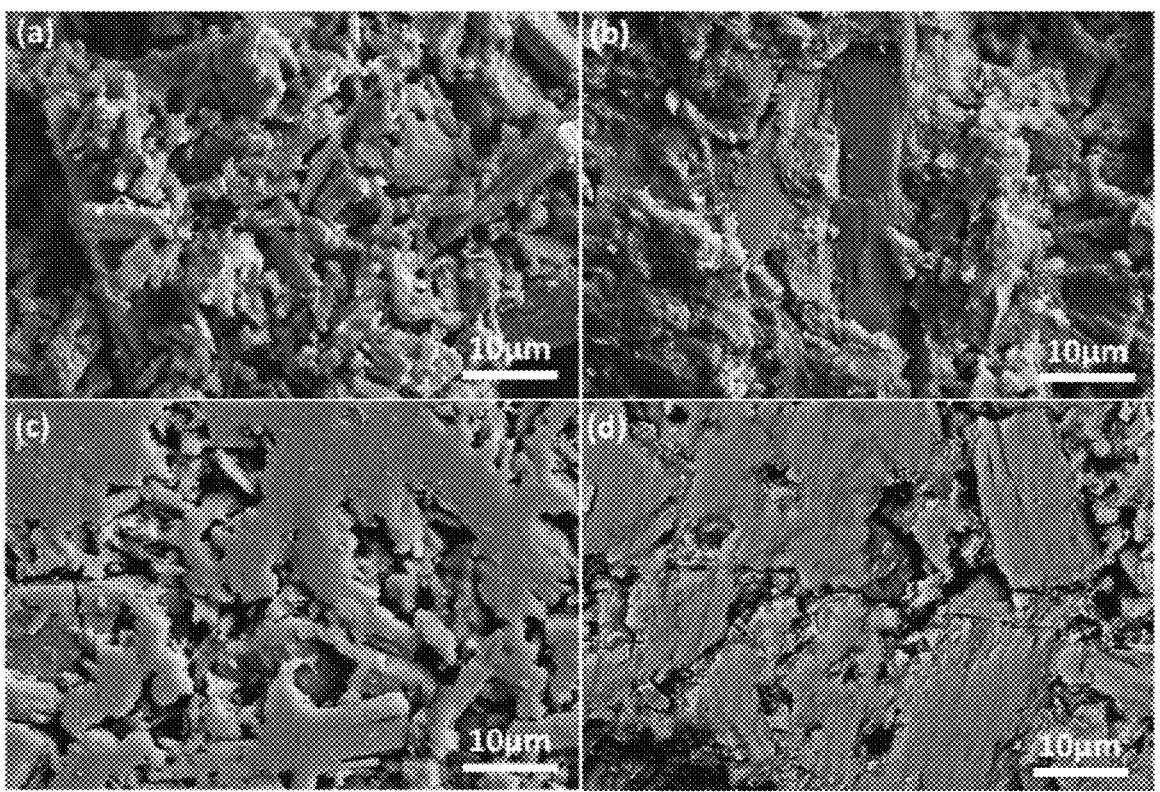
FIGS. 4A-4D show: fracture surfaces of (4A) HTS1150 and (4B) H1150LTS samples, and crack propagation path of (4C) HTS1150 and (4D) H1150LTS samples.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally includes up to plus or minus 10% of the indicated number. For example, "about 10%" may indicate a range of 9% to 11%, and "about 20" may mean from 18 to 22. Preferably "about" includes up to plus or minus 6% of the indicated value. Alternatively, "about" includes up to plus or minus 5% of the indicated value. Other meanings of "about" may be apparent from the context, such as rounding off, so, for example "about 1" may also mean from 0.5 to 1.4.

Calcium silicate bioactive materials, including glasses, glass ceramics and ceramics, are a new generation of biomaterials which can support the body's effort to repair itself, and which are biochemically compatible with natural bone. A common characteristic of these bioactive materials is their release of Si and Ca ions, henceforth referred as "soluble factors". The soluble factors released from the calcium silicate bioactive materials can: (a) form a biologically active carbonated apatite layer on the implant surface creating strong bone-implant interfaces and providing structural support (osteoconductivity) for healing, and (b) enhance cell activity, including proliferation, and osteogenic differentiation (osteoinductivity), and in vivo new bone formation in direct contact with the material. Within this class of materials, 45S5 bioglass is known to have good biocompatibility, osteoinductivity and low toxicity; however, the mechanical properties of 45S5 bioglass mismatch with human cortical bone due to high brittleness, low mechanical strength (42 MPa in bending/tensile strength) and low fracture toughness (0.6 MPa·m$^{1/2}$). Thus, 45S5 bioglass cannot be used for load-bearing applications. This drawback severely limits the use of 45S5 bioglass to very few clinical applications. In contrast, crystalline $CaSiO_3$ ceramics, even though they possess better mechanical strength (ca. 50 MPa in bending strength) and toughness (0.9 MPa·m$^{1/2}$), lack the favorable biological properties of the bioglasses. Therefore, the development of bioactive materials that have bone-like mechanical properties, including compressive strength of 130-290 MPa, bending strength of 60-150 MPa and fracture toughness of 2-12 MPa·m$^{1/2}$ together with favorable biological properties of osteoinductivity, biocompatibility and low toxicity are urgently sought as bone replacement implants.

Bone replacement implants having lower mechanical strength than that of natural bone can fail under mechanical loads. High Temperature Sintering (HTS) is an effective way to both densify and strengthen ceramic materials. However, silicate ($MSiO_3$) ceramics are difficult to completely densify with HTS because secondary grain growth rapidly encapsulates pores within each grain thereby limiting the density and mechanical strength to relatively low values. In general, ceramics are known to be brittle (not tough) materials because of their lack of ductility. When a crack develops in an implant that has a lower fracture toughness than that of natural bone, the crack will propagate faster than a crack in the bone itself, causing failure.

Despite not possessing an intrinsic toughening mechanism, the toughness of these ceramics can be increased by the addition of reinforcing phases that contribute to extrinsic toughening. In addition, a variety of calcium silicate-based ceramics have been prepared with the goal of improving mechanical properties of these implant candidates further by investigating the influence of different processing methods. These studies are summarized in the following table:

| Material | Forming Method | Heat treatment | Phases | Relative density (%) | Bending Strength (MPa) | Compressive Strength (MPa) | Elastic modulus (GPA) | Fracture Toughness (MPa · m$^{1/2}$) |
|---|---|---|---|---|---|---|---|---|
| Xonotlite | (UP) 50 Mpa + (CIP) | T$_{sintering}$ 1100° C. t$_{holding}$ = 24 h T$_{annealing}$ | W | 65 68 | 42 51 | — | — | — |
| Synthetic W precipitation | (UP) 14 Mpa + (CIP) | 900° C. t$_{holding}$ = 3 h 1100° C. t$_{holding}$ = 3 h t$_{holding}$ = 5 h 1200° C. t$_{holding}$ = 3 h | — | 65 81.4 89.5 82.4 | 3PB 5.4 65.9 95 53.5 | | | — |
| Mineral W Mineral W milled Synthetic W Solid state | (UP) 500 MPa | 600° C./min 1400° C. t$_{holding}$ = 2 h | PsW | — | — | 26 48 42 | — | — |
| Synthetic W chemical precipitation | — — | SPS 150-200° C./min 750° C., 150-200° C./min | Amorph -W | 89.35 75.6 | 3-PB 190 100 | — — | — — | SENB 1.67 1.52 |
| Synthetic W chemical precipitation | — — | SPS 150-200° C./min 950° C. SPS 150-200° C./min 970° C. | W PsW | 95 99 | 3-PB 290 3-PB 65 | — | — — | SENB 2.0 SENB 0.5 |
| W W, 20 wt % HA | — | SLS | — | 82.96 92.26 | — | 18.19 27.28 | 0.12 0.16 | Vickers 1.19 1.43 |
| Synthetic W (precipitation) W, W 50 wt % β-TCP | (UP)10 Mpa + (CIP) 200 MPa | HTS 2° C./min 1100° C. t$_{holding}$ = 5 h | W ½ W, ½ β-TCP | 75.7 81.3 | 3PB 35.1 61.7 | — | — | Not mentioned 0.6 0.9 |
| Synthetic W (sol-gel) CaSiO$_3$ CaSiO$_3$-5 mol % ZnO CaSiO$_3$-5 mol % ZrO$_2$ | (UP) 200 MPa | 5° C./min 950° C. t$_{holding}$ = 0.5 h | — | — | 28 36 42 | | 8 11 17.5 | — |

UP: Uniaxial Press;
CIS: Cols Isostatic Press;
HTS: conventional High Temperature Sintering;
SLS: Selective Laser Sintering;
SPS: Spark Plasma Sintering:
SENB: Single-Edge Notch Beam;
TCP: tricalcium phosphate;
HA: hydroxyapatite;
W: wollastonite Conventional high temperature sintering (HTS) produced materials with three-point bending strength of 51 MIPa or 95 MPa and compression strength of 48 MPa respectively. Sparkplasma sintering (SPS) methods reported materials with three-point bending strength of 190M Pa, and fracture toughness of 1.67 MIPa·m$^{1/2}$. Another SPS publication reported materials with bending strength of 290 MIPa, and fracture toughness of 2 MPa·m$^{1/2}$. Adding hydroxyapatite (HA) as a reinforcing phase provided a material having a compressive strength of 27 MPa and fracture toughness of 1.43 MPa·m$^{1/2}$. CaSiO$_3$/β-TCP (tricalcium phosphate) composites exhibited a bending strength of 71.7 MPa and a fracture toughness of 0.9 MPa·m$^{12}$. Partial substitution of ZnO and ZrO$_2$ for wollastonite produced material with 36 MPa and 42 MPa three point bending strength respectively. Thus, although some improvements in mechanical properties have been reported, either the essential mechanical properties of the resulting composites have not been presented in those studies, or these modifications fail to provide both the strength and toughness required for match of the ceramic composites with the properties of natural bone. The one exception appears to be CaSiO$_3$ ceramics processed by Spark Plasma Sintering (SPS), which achieved relative densities as high as 95% with the composites possessing promising mechanical properties for bone replacement, due to suppression of rapid grain growth (average grain size of 0.6 m) during sintering. However, the limitations of this method, including high cost, make SPS impractical for producing bone implants on a commercial scale.

The present inventors have recently developed a new densification technique called Low Temperature Solidification (LTS) that proceeds by carbonation, which can improve the strength of calcium silicate-based ceramics as disclosed in U.S. Patent No. 2014/0093659 A1. The method involves passing a gas through a porous matrix, where the gas conveys reactants to a wetted ceramic matrix surface. During the LTS process, rapid gaseous diffusion takes place throughout a porous material preform, and reactive sites on the wetted porous matrix surface react with CO$_2$ to form products that fill at least a portion of the interstitial spaces.

A schematic diagram of the LTS process is shown in FIG. 1. During the LTS process, a thermodynamically favorable carbonation reaction occurs as shown in the equation below:

$$CaSiO_{3(s)}+CO_{2(g)}=CaCO_{3(s)}+SiO_{2(s)} \Delta H°=-87 \text{ kJ/mol } CO_2$$

Precipitation of CaCO$_3$ and SiO$_2$ inside the compact's pores densifies the CaSiO$_3$ porous compact. Carbonation of CaSiO$_3$ under relatively low temperature and pressure (<100° C., ca. 2.36 atm (20 psig) CO$_2$) conditions has been demonstrated, resulting in monolithic ceramics having remarkable mechanical properties. LTS-processed CaSiO$_3$ ceramics have a carbonation degree of ca. 47.5%, and the relative density increased to ca. 81% versus ca. 64% prior to carbonation, achieving a compressive strength of 160±17 MPa which is comparable to conventional high temperature sintered CaSiO$_3$ ceramics.

It has now been discovered that LTS can be used on HTS-processed calcium silicate to increase the density of calcium silicate ceramics thereby improving microstructural and mechanical properties under relatively mild conditions. Thus, the LTS method increases the density of HTS-processed calcium silicate and enhances the mechanical properties of calcium silicate ceramics in a cost-effective manner to achieve the mechanical properties of cortical bone.

The Influence of Densification Method on the Structure and Mechanical Properties of Calcium Silicate Composites Experimental Strategy Experiments were performed to understand the effect of the combination of High Temperature Sintering (HTS) and Low Temperature Solidification (LTS) processes together on microstructure and mechanical properties of CaSiO$_3$ samples. The LTS carbonation process was performed on CaSiO$_3$ green bodies and HTS processed CaSiO$_3$. HTS CaSiO$_3$ and LTS CaSiO$_3$ served as controls. Hereafter, the term "HLTS" is employed to designate CaSiO$_3$ ceramics prepared by high temperature sintering followed by low temperature solidification. The numbers "1100", "1150", "1200" used as part of the HTS and HLTS acronyms indicate the temperatures applied during sintering. Terminology used to define processed CaSiO$_3$ ceramics is presented in the table below:

| Sample | HTS $T_{sintering}$ (° C.) | LTS $T_{carbonation}$ (° C.), P (psi) |
|---|---|---|
| HTS1100 | 1100 | — |
| HTS1150 | 1150 | — |
| HTS1200 | 1200 | — |
| LTS | — | 90, 20 |
| H1100LTS | 1100 | 90, 20 |
| H1150LTS | 1150 | 90, 20 |
| H1200LTS | 1200 | 90, 20 |

Crystalline phase analysis, the degree of carbonation, porosity and pore size distribution, Brunauer-Emmett-Teller (BET) specific surface area, and SEM were monitored to evaluate physical and chemical characterization of samples after carbonation. Compressive strength, three-point flexural strength, hardness and fracture toughness of ceramic compacts were tested to evaluate mechanical properties of CaSiO$_3$. Physical and chemical characteristics of HTS and/or LTS processed CaSiO$_3$ ceramics and their relation to observed mechanical properties were assessed. Effectiveness of the LTS process on the densification of a porous HTS CaSiO$_3$, and its contribution to mechanical properties of CaSiO$_3$ were evaluated.

The phase composition of green, HTS, LTS, and HLTS CaSiO$_3$ samples was identified using x-ray diffraction. Before carbonation, wollastonite (a low temperature phase of CaSiO$_3$) was observed for green and sintered samples at 1100 and 1150° C. Pseudowollastonite (PsW, high temperature phase of CaSiO$_3$) was the only detected primary phase for samples sintered at 1200° C. as a result of phase transformation from wollastonite to pseudowollastonite known to occur typically at temperatures of 1125±10° C. After carbonation, all emerging peaks corresponded to reaction product CaCO$_3$ phases: calcite, aragonite and vaterite. The following table summarizes the quantitative phase analysis by Rietveld refinement.

| Sample | Wollastonite CaSiO$_3$ | Pseudowollastonite (PsW) CaSiO$_3$ | Calcite CaCO$_3$ | Aragonite CaCO$_3$ | Vaterite CaCO$_3$ | SiO$_2$ |
|---|---|---|---|---|---|---|
| Raw | 97 | 0 | 1.1 | 0 | 0 | 1.6 |
| HTS1100 | 97 | 0 | 0 | 0 | 0 | 3 |

-continued

| Sample | Wollastonite CaSiO$_3$ | Pseudowollastonite (PsW) CaSiO$_3$ | Calcite CaCO$_3$ | Aragonite CaCO$_3$ | Vaterite CaCO$_3$ | SiO$_2$ |
|---|---|---|---|---|---|---|
| HTS1150 | 90 | 10 | 0 | 0 | 0 | 0 |
| HTS1200 | 3 | 97 | 0 | 0 | 0 | 0 |
| LTS | 40 | 0 | 22.5 | 28 | 4.5 | 5 |
| H1100LTS | 48 | 0 | 15 | 0 | 32 | 5 |
| H1150LTS | 43 | 9 | 14 | 0 | 31 | 3 |
| H1200LTS | 0 | 86 | 4 | 0 | 10 | 0 |

The primary CaCO$_3$ polymorphs formed during carbonation were (a) 'calcite' and "aragonite" for only LTS-processed samples, (b) "calcite" and metastable "vaterite" for sintered-followed-by-LTS-processed samples. Vaterite is the least stable polymorph of CaCO$_3$; calcite is the most stable one. During the reaction, the initially formed vaterite was expected to convert into aragonite or calcite. It has been reported that when vaterite is exposed to water, it can transform to more stable aragonite or calcite. Without wishing to be bound by any particular theory, it is believed that the formation of different CaCO$_3$ phases arise due to the presence of free hydroxyl groups originally present in green CaSiO$_3$, and that these hydroxyl groups are removed during the course of sintering. While a vaterite phase is present with calcite for sintered samples, aragonite takes the place of vaterite in the LTS-reacted green CaSiO$_3$. Thus, it is believed that during carbonation the presence of hydroxyl groups in the CaSiO$_3$ is one of the factors determining the specific form of the reaction products. After LTS reaction, no increase in the SiO$_2$ product peak was detected. The carbonated green CaSiO$_3$(LTS) showed a degree of carbonation of 52% whereas pre-sintering the wollastonite prior to carbonation (HLTS) reduced the degree of carbonation to 45-12%, depending on the sintering temperatures in the range of 1100-1200° C. The degree of carbonation decreased with increasing sintering temperature of CaSiO$_3$, as evidenced by the intensity of the carbonate peaks. It is believed that the degree of carbonation decreased with sintering temperature as a result of a decrease in surface area of the sintered material.

Thermal gravimetric analysis (TGA) of CaSiO$_3$ before and after carbonation reaction shows a weight loss observed up to 200° C. correlated with removal of physically adsorbed water, while weight loss between 200-800° C. corresponded to decomposition of CaCO$_3$. HTS samples showed no weight loss in the latter range, indicating there was no calcium carbonate prior to the reaction. Thermal analysis confirmed the presence of a carbonate phase after LTS reaction. The extent of carbonation of the reacted samples was maximum for carbonated green CaSiO$_3$(LTS) and decreased with increasing sintering temperature for HLTS samples. The degree of carbonation (as molar CaCO$_3$ percentage) in the HTS, LTS, and HLTS samples was measured by TGA, net weight gain, and calcimeter methods:

| | $\lambda_{TGA}$ | $\lambda_W$ | $\lambda_C$ |
|---|---|---|---|
| LTS | 52.98 | 52.68 | 52.59 |
| H1100LTS | 45.55 | 46.95 | 44.38 |
| H1150LTS | 36.36 | 37.3 | 36.69 |
| H1200LTS | 13.51 | 13.77 | 14.93 |

For reacted samples, while the degree of carbonation for green CaSiO$_3$(LTS) was 52%, this value decreased to 46, 36, and 12% with increasing sintering temperature for pre-sintered samples. A decrease in the degree of reaction with increase in sintering temperature correlates with a reduction in surface area of the CaSiO$_3$ compact that interacts with reactant gas. Thus, the mass gain observed after LTS reaction arises from the carbonation reaction.

Relative density data of HTS-only samples showed that conventional high temperature sintering makes only a limited contribution to the further densification of 65% dense green body of CaSiO$_3$, producing only ca. 3% increase in relative density. Therefore, HTS is an inefficient method to densify CaSiO$_3$. This data is consistent with literature reports. When LTS carbonation was applied to green and sintered CaSiO$_3$, relative density increased up to 85%. The degree of carbonation was the main reason for a steep increase in relative density. In addition, compared to green CaSiO$_3$ the carbonation percentage decreases (from 52.7 to 37%) with increasing pre-sintering temperature; however, the relative density decrease was negligible for LTS-only, H1100LTS and H1150LTS samples, with values ranging from 84.85 to 83.62% (versus the initial 85%). Thus, other factors contribute to an increase in relative density.

The pore size distribution of HTS, LTS and HLTS samples is presented in the table below:

| | Pore size (µm) | |
|---|---|---|
| Temperature (° C.) | HTS | LTS/HLTS |
| RT | — | 0.025-0.034 |
| 1100 | 0.598 | 0.094-0.057 |
| 1150 | 1.279 | 0.187-0.246 |
| 1200 | 2.718 | 1.655-1.023 |

For HTS-only samples, the pore size increased from 0.6 to 2.7 m with increasing sintering temperature ranging from 1100 to 1200° C. After carbonation of green CaSiO$_3$ (LTS-only), the pore size decreased substantially to 0.025-0.034 µm. For HLTS samples, the pore size distribution decreased in proportion to the degree of carbonation of the sintered CaSiO$_3$. The pore size distribution was 0.0094-0.057 m for H1100LTS samples, 0.187-0.246 m for H1150LTS samples, and 1.655-1.023 m for H1200LTS samples. For HTS samples, porosity decreased from 34 to 31% with increasing sintering temperature. The pore size increase together with a negligible porosity decrease indicated that grain growth was primarily responsible for morphology modification during sintering. Porosity data also proved that CaSiO$_3$ does not densify effectively using only HTS processing alone. The porosity of LTS-only samples decreased to 14.6%. For HLTS samples, the porosity reduced to 15.35-27.33% depending on the initial HTS sintering temperature and the degree of subsequent LTS carbonation. During carbonation, a decrease in pore volume and pore size indicated that reaction products filled the pores and narrowed the pore size. Carbonation of green CaSiO$_3$ (LTS-only) decreased the pore volume, and the average pore size narrowed to mesopore dimensions (2-50 nm). For sintered-then-carbonated (HLTS) samples, both pore size and pore volume decreased compared to HTS-only samples, in proportion to their degree of carbonation. Thus, porosimetry data confirmed the densification of samples following the carbonation process.

The BET surface area of green $CaSiO_3$ powder was observed to be 1.91 $m^2$/g. For HTS samples, the surface area decreased with increasing sintering temperature (0.93, 0.40, 0.14 $m^2$/g, respectively for sintering at 1100, 1150 and 1200° C.). A reduction in surface area of HTS samples arises from coarsening of particle and pore surfaces, and an increase in grain and pore size. Surface area of LTS-only samples was 0.94 $m^2$/g. The BET surface area of HLTS samples increased to 2.10 and 0.75 and 0.38 $m^2$/g, respectively, with increasing sintering temperature versus pre-carbonation values (HTS-only samples). Increase in surface area was proportional to the degree of carbonation. Without wishing to be bound by any particular theory, it is believed that the surface area change after carbonation arises from formation of reaction products, including $CaCO_3$ and silica-rich leached layers, and a decrease in the pore size and the porosity as the pores are (partially) filled with these reaction products. Reaction products tend to increase the surface area due to small $CaCO_3$ particle development and formation of leached layers. Decrease in final pore size and volume as a result of the accumulation of reaction products on the surface of pore walls throughout the pore network decreases the surface area. BET data also indicates that the degree of carbonation was proportional to the surface area of the starting material. For HLTS composites, sintering conditions prior to carbonation correlate with a reduction in the reaction percentage and a decrease in surface area of $CaSiO_3$ with increasing sintering temperature. During carbonation, the layer of reaction products, including $CaCO_3$ and silica-rich amorphous phases, surrounding the core $CaSiO_3$ phase become thicker as the reaction progresses, which further slows the carbonation reaction due to limited diffusion of Ca ions through the silica-rich layer. These results indicate that surface area is an important parameter affecting the degree of reaction during carbonation.

Back Scattered Electron (BSE) images collected from HTS, LTS and HLTS samples are shown in FIGS. 2A-2C and 3A-3D. Both mesopores and macropores (black regions) having consistent pore size as measured by a porosimeter were observed in these micrographs. For HTS samples (FIGS. 2A-2C), when sintering temperature was increased to 1150° C., the morphology changed to a continuous network of solid $CaSiO_3$ (grey) and porous (black) while the acicular nature of the wollastonite mineral starting material was still maintained. With further increase in sintering temperature to 1200° C., grain and pore size shows that a coarsening (rapid grain growth) mechanism became predominant for $CaSiO_3$ compacts and the particle morphology changed to a honeycomb-like structure. For LTS samples, pore filling reaction products were clearly observed. The core-shell structure produced by LTS included cores of partially carbonated acicular $CaSiO_3$ grains surrounded by $SiO_2$-rich layers that were in turn encapsulated by $CaCO_3$ particles. For HLTS samples, the same core-shell structure was observed, and with increasing sintering temperature from 1100 to 1150° C. a microstructure having more pronounced phase boundaries appeared. Phases having a different shade of gray due to differences in their average atomic number could be identified: (a) the brightest regions were unreacted $CaSiO_3$ cores, (b) surrounded by a dark gray $SiO_2$-rich amorphous phase, (c) surrounded by a $CaCO_3$ phase in medium gray shade, and (d) black regions were pores. EDS chemical maps also confirmed this core-shell structure and arrangement of each compound after LTS reaction. Following carbonation, the presence of reaction products filling the pores of $CaSiO_3$ was proportional to the degree of reaction. Carbonation of sintered samples created core-shell structures having more discrete phase boundaries due to the sintering of small $CaSiO_3$ particles to larger particles during heat treatment. Per the EDS maps of carbonated samples, in addition to $CaCO_3$ phase regions, $SiO_2$-rich regions could also be clearly identified in the microstructure, even though they could not be observed using X-ray diffraction. Therefore, the silica-rich layer that forms is an amorphous phase.

Mechanical Properties

During strength tests, samples showed brittle behavior with a steep decline in stress after ultimate strength was reached. HTS-only samples showed a gradual increase in average strength from 41.5 to 129.7 MPa with increasing sintering temperature from 1100 to 1150° C. However, the strength decreased to 112.9 MPa with a further sintering temperature increase to 1200° C., demonstrating that sintering at that temperature fails to contribute additional strength. For comparison, the average strength of carbonated green $CaSiO_3$(LTS-only) was measured as 276.7 MPa. For the HLTS samples, the average strength was recorded as 253.4, 279.2 and 120 MPa for sintering temperatures of 1100, 1150 and 1200° C., respectively. The large decrease in the mechanical strength of $CaSiO_3$ compacts sintered at 1200° C. and then carbonated (H1200LTS) can be attributed to abnormal grain growth coupled with a negligible contribution from the carbonation process due to a substantial decrease in the surface area of the pre-sintered samples. Compression strength changed depending on the relative density of the processed samples. As expected, compression strength increased with increasing relative density.

The average elastic modulus of compression was also determined for the samples. For HTS-only samples, modulus increased from 2.3±0.2 GPa to 17.4±1 GPa with increasing sintering temperature. The modulus of subsequently carbonated (HLTS) samples showed a slight decrease with increased sintering temperature from 18.9±2 to 18.7±1.5 GPa. For comparison, LTS-only samples showed an average elastic modulus of 20.7±2.5 GPa. An elastic modulus increase was expected, which varied linearly with decreasing porosity and increasing sintering temperature. Therefore, increase in the elastic modulus by HLTS processing can be attributed to densification (decrease in porosity) by sintering and introduction of reaction products into the pores of $CaSiO_3$ compacts. Elastic moduli of processed $CaSiO_3$ samples are comparable with the modulus of cortical bone which is in the range of 3-30 GPa.

Flexural strength of HTS, LTS, and HLTS samples showed a trend similar to the compressive strength data. By applying HTS, a maximum bending strength of 47.2±2.5 MPa was achieved for a sintering temperature of 1150° C. The strength increased to 70.0±2.6 MPa for carbonation of green $CaSiO_3$ (LTS-only) and 65.5±2.1 MPa for carbonation of sintered $CaSiO_3$ (HLTS). Both compressive and flexural strength of the carbon-ated samples surpassed those of the corresponding sintered $CaSiO_3$ samples (HTS-only).

Vickers hardness of HTS, LTS, and HLTS samples was also measured. With increasing temperature of HTS-only samples, hardness increased from 0.3 to 0.79 GPa. Hardness of LTS-only samples was 2.32 GPa, while hardness of HLTS samples was in the range of 1.98-0.75 GPa showing a decrease with decreasing degree of carbonation. The increase in hardness was proportional to the decrease in porosity as a result of sintering and carbonation. Carbonated green $CaSiO_3$ achieved the highest hardness value, as expected due to formation of a high density aragonite phase instead of the lower density vaterite phase observed upon sintering.

Fracture Toughness of processed $CaSiO_3$ ceramics was also determined. A load-time analysis showed that the requirement of crack stabilization was met. This test verifies that slow crack growth behavior was evident. Whereas the fracture toughness of HTS1150 samples ($CaSiO_3$ sintered at 1150° C.) was 0.96±0.05 Mpa√m, H1150LTS samples ($CaSiO_3$ sintered at 1150° C. and then carbonated) reached the maximum toughness value of 1.87±0.13 Mpa√m. LTS-only samples also achieved similarly high toughness (1.76±0.2 Mpa√m). The fracture toughness by carbonation of green and sintered $CaSiO_3$ ceramics was observed to be close to that of cortical bone, and about two times that of conventionally sintered $CaSiO_3$. FIGS. 4A-4D show fracture surfaces with microstructure sections perpendicular to the fracture surface (in the direction of crack propagation) of HTS and HLTS samples after fracture toughness testing. As expected, the samples showed the characteristic brittle fracture behavior of ceramic materials, failing catastrophically after a small amount of elastic strain. As can be seen from the SEM micrographs, while the fracture mode of $CaSiO_3$ was cleavage (transgranular), $CaCO_3$ showed intergranular fracture. After carbonation of green (LTS-only) and sintered $CaSiO_3$ (HLTS), an increase in fracture toughness is associated with crack deflection in the presence of pore-filling $CaCO_3$ particles, which show intergranular fracture behavior. The following table summarizes the effect of HTS, LTS, and HLTS processes on the mechanical properties of $CaSiO_3$.

actually approached the relative density of LTS-only $CaSiO_3$ and thus both LTS and HLTS samples achieved high strength values. This finding points to other mechanisms contributing to densification of HLTS samples to reach similar densification and mechanical properties as LTS-only $CaSiO_3$. These data indicate that the relative density of HLTS $CaSiO_3$ increases via at least two other factors, including:

(a) The variation in the polymorphic form of carbonate phases formed during the reaction. After carbonation, aragonite and calcite phases form on green $CaSiO_3$; however, vaterite takes the place of aragonite during the carbonation of pre-sintered $CaSiO_3$. Since vaterite has a lower density (2.645 $g/cm^3$) than that of aragonite (2.95 $g/cm^3$), when vaterite is formed instead of aragonite, the relative density of the composite increases by about 2%. For example, H1150LTS samples have a relative density of 83.6%. However if aragonite forms on those samples as found in LTS-only samples, the relative density of the composite would be 81.4%.

(b) The high temperature sintering process contributes to densification of $CaSiO_3$ to a minor degree, even though it is not an effective way to fully densify $CaSiO_3$. Especially at a sintering temperature of 1150° C. which was observed to be the highest temperature before coarsening initiates, the sintering process increased the relative density by ca. 3%. Briefly, the data showed that even though there was a decrease in the degree of reaction of HLTS samples compared to LTS-only samples, the observed relative density difference (ca. 5%) arose from a lower degree of carbonation of HLTS samples which was compensated for by the HTS process and formation of the vaterite polymorph. Further, due to their similar relative densities, similarly high

| | Degree of Carbonation ($\lambda_{TGA}$) mole % | Relative Density % | Open Porosity % | Compressive Strength MPa | Elastic Modulus GPa | Bending Strength MPa | Vickers Hardness GPa | Fracture Toughness Mpa√m |
|---|---|---|---|---|---|---|---|---|
| HTS1100 | 0 | 65.53 ± 0.51 | 34.20 | 42.66 ± 3.67 | 2.29 ± 0.2 | 13.40 ± 1.33 | 0.30 ± 0.01 | — |
| HTS1150 | 0 | 67.62 ± 0.19 | 32.22 | 129.97 ± 5.8 | 14.26 ± 0.4 | 47.15 ± 2.64 | 0.60 ± 0.02 | 0.96 ± 0.05 |
| HTS1200 | 0 | 67.18 ± 0.22 | 32.71 | 113.9 ± 8.25 | 17.38 ± 1.0 | 41.31 ± 0.51 | 0.79 ± 0.04 | — |
| LTS | 52.68 ± 0.42 | 84.89 ± 0.21 | 14.59 | 276.68 ± 38.7 | 20.69 ± 2.5 | 70.02 ± 2.59 | 2.24 ± 0.07 | 1.76 ± 0.19 |
| H1100LTS | 45.00 ± 0.78 | 83.36 ± 0.64 | 15.35 | 253.4 ± 12.76 | 18.88 ± 2.1 | 61.01 ± 3.51 | 1.98 ± 0.03 | 1.61 ± 0.15 |
| H1150LTS | 37.13 ± 1.08 | 83.48 ± 0.76 | 15.78 | 279.24 ± 31.05 | 18.83 ± 2.7 | 65.52 ± 2.1 | 1.71 ± 0.07 | 1.87 ± 0.13 |
| H1200LTS | 12.56 ± 1.34 | 71.78 ± 0.57 | 27.33 | 120.08 ± 26.7 | 18.68 ± 1.5 | 34.06 ± 3.08 | 0.75 ± 0.01 | — |

The above experimental results indicate that carbonation improves the densification of sintered $CaSiO_3$ ceramics and so enhances mechanical properties of $CaSiO_3$ ceramics, and achieves mechanical properties similar to those of cortical bone. This process is also cost effective.

Carbonation of (a) green $CaSiO_3$ compacts (LTS-only), (b) $CaSiO_3$ sintered at 1100° C. (H1100LTS) and (c) $CaSiO_3$ sintered at 1150° C. (H1150LTS) provided similarly enhanced densification and mechanical strength and toughness. Actually, HLTS samples possessed a relatively lower degree of carbonation compared to LTS-only samples (52.7%); further, their degree of carbonation decreased from 45 to 12.6% with increasing sintering temperature. The reduction in the degree of carbonation can be explained by a decrease in the surface area of $CaSiO_3$ upon increasing sintering temperature thereby reducing the surface available to produce further reaction products. As a result of a lower degree of carbonation, it would be expected that HLTS samples would have lower densification and less enhancement in mechanical properties compared to LTS-only samples. However, the relative density of HLTS $CaSiO_3$ mechanical strengths were reached with LTS-only, H1100LTS and H1150LTS samples.

Improvement in fracture toughness was achieved by all carbonated samples, LTS-only, H1100LTS, and H1150LTS, compared to the HTS-only sample. Thus the carbonation reaction creates toughening phases that can activate extrinsic toughening mechanisms in the material structure. Without wishing to be bound by any particular theory, it is believed that the pore-filling $CaCO_3$ phase has crack energy absorbing properties. The 95% improvement of fracture toughness by carbonation is believed to be due to crack deflection by carbonation reaction products.

Depending on the pre-sintering temperature prior to carbonation, differences in pore sizes and microstructure were detected. For LTS-only, H110LTS and H1150LTS, all samples achieved similarly improved densification and also achieved the mechanical compatibility requirements; however, H1150LTS samples having a relatively larger pore size and more uniform phase distribution in the microstructure constitute a more promising material for biomedical applications. Large pores are better for tissue growth and vascularization. In addition, variation in response in biological medium is also expected due to differences in their degree of carbonation and the solubility of reaction products.

The present $CaSiO_3$ composites produced by carbonation of sintered $CaSiO_3$ have advantages for biomedical applications versus SPS-densified $CaSiO_3$ in several aspects. First, grain size is about 0.6 m using SPS, while grain size is in the range 5-15 μm using the present carbonation process of sintered composites. Nano-scale materials are not promising for biomedical applications due to their higher surface area which has a higher potential dissolution rate, corresponding to a higher, potentially toxic, release of inorganic ions. Second, considering that both SPS- and the present carbonation process-produced materials have mechanical properties compatible with cortical bone, those materials characterized by a higher porosity and larger pore size would be preferred over denser material having a smaller pore size. Third, the high cost and shape limitations intrinsic to the SPS technique makes it a less promising method for production of a variety of shaped bone substitutes. In contrast, the present carbonation process is cost effective, and allows production of any shaped material.

Another advantage of the present technique is the ability to tune the microstructural and mechanical properties of these composites by adjusting the degree of carbonation, the pre-sintering temperature and the initial particle size and pore size of $CaSiO_3$ compacts, which in sum provide the capability of producing a customized implant to obtain the best fit with host bone, depending on bone type, gender and age. Further, the inventive carbonation process disclosed herein demonstrates the robust production of $CaSiO_3$—$CaCO_3$—$SiO_2$ composites having high strength and toughness, as well as tunable density strength properties.

In summary, applying a carbonation process to pre-sintered $CaSiO_3$ compacts substantially improved densification, compression strength, flexural strength, and fracture toughness versus sintered-only $CaSiO_3$ ceramics. An increase in the relative density from 68.5 to 84.3 g/cm³, indicates that the compacts were substantially densified after carbonation. A compression strength of 279 MPa, bending strength of 65.5 MPa, and fracture toughness of 1.87 $MPa \cdot m^{1/2}$ were achieved with the H1150LTS samples (sintered at 1150° C. and then carbonated). The dense ceramic composites produced by the carbonation of sintered $CaSiO_3$ (particularly H1150LTS) have compressive strength and toughness properties similar to those of human cortical bone and provide useful candidates for bioactive implant materials.

As demonstrated above, an important aspect of the present inventive composite material and it's method of preparation is the unexpected result that, when the ceramic material is first sintered and then treated under LTS conditions, the strength of the resulting material is observed to increase. Further, the opposite ordering of sintering and LTS treatment steps produces a much weaker material. This result is important to the fabrication of all carbonate bonded materials. Without wishing to be bound by any particular theory, it is believed that the following processes are involved in composite material strengthening. Carbonation of a ceramic material provides an initial strength that is reasonable. However, when such a carbonated material is heated at high temperature, or sintered, the carbonate decomposes and only a porous bond remains that is no denser or stronger than the initial material. However, when a ceramic material is sintered followed by low temperature solidification (LTS) carbonation as a final step, the LTS carbonation decreases the porosity in the material and reinforces the sintered structure, such that the decrease in porosity strengthens the material, and as the porosity percentage decreases strength exponentially increases. In this way, the strength and porosity data can be explained and exploited to advantage. Further, simply in terms of bond strength, oxide bonding is stronger than carbonate bonding, which is why carbonate materials like calcite (Moh's hardness=3) are soft materials, but oxide materials like quartz (Moh's hardness=7) or alumina (Moh's hardness=9) are much harder. This is also why the presently described calcium silicate is stronger than all fired or sintered materials known in the literature. Others have been able to make certain materials less porous, and thereby increase strength, but apparently this is only possible when the material is hot pressed. Hot pressing is very expensive, and the shapes available using such a method are limited. In contrast, the presently disclosed method is both inexpensive and amenable to fabrication of materials of almost any size or shape.

The Modulation of Soluble Factors Via Carbonation of $CaSiO_3$ Ceramics

Soluble factors, both organic and inorganic, can affect all stages of bone generation. Bone morphogenetic proteins (BMPs) are well known organic soluble growth factors. Depending on the type, BMPs may possess osteoinductive (new bone formation) activity or only osteoconductivity (structural support). Similarly, Ca and Si ions are inorganic soluble factors released from calcium-silicate based materials including bioglasses, glass-ceramics and ceramics. Depending on the concentration of Ca and Si released from the implant material, these inorganic factors can induce osteoinductivity or only osteoconductivity. Osteoconductive materials provide a scaffold upon which new bone grows. In the case of bone injury, if a hard tissue gap is created, new bone growth is supported only along the bone-implant interface. Osteoconductive activity is observed on bone implant materials with high biocompatibility including hydroxyapatite (HA), tricalcium phosphate, and calcium-silicate ceramics. Osteoconductive calcium-silicate glasses and ceramics form an apatite-like layer on the implant surface as a result of Ca and Si ion release from the material. This apatite-like layer provides strong bonding at the bond-implant interface.

Osteoinduction (osteogenesis) is a basic biological mechanism that commonly occurs in the course of bone healing after a fracture. Upon stimulation, an undifferentiated mesenchymal cell (hMSC) transforms into a preosteoblast and provides regeneration of the bone tissue. This important process for bone healing is also referred to as bone induction. Unlike osteoconductivity, an external material, such as an implant surface, is not a prerequisite for bone induction. However, studies revealed that some materials accelerate new bone formation by chemically stimulating undifferentiated (mesenchymal) cells located near the implant to differentiate into bone progenitor cells. Therefore, these materials are defined as "osteoinductive materials". Introducing osteoinductive implants provides faster bone healing at the site of injury by stimulating the body's own repair mechanisms to regenerate bone. Osteoinductive materials, in addition to their bonding to bone, in contrast to osteoconductive materials, also have the ability to form bonds with soft tissues (ectopic sites), such as muscles. Moreover, the use of osteoinductive implants is crucial where the bone defects are large, since the natural migration of osteoprogenitor cells does not suffice for fracture healing near the center of the implants. The above-described HLTS process provides such osteoinductive materials to repair bone defects resulting from injury and disease and to expedite the healing process.

45S5 bioglass is a well-studied bioactive glass ceramic composition, unique by virtue of its osteoinductivity. 45S5 bioglass releases Si ion in a concentration of <19 ppm in the medium, which stimulates (activates) osteogenic differentiation (osteogenesis or osteoinduction). Bioglasses can also be non-osteoinductive if the release of soluble factors is not in the right range, due to a lack of ionic stimuli on the one hand (insufficient soluble factor release) or release excessively high and toxic ionic concentrations on the other hand. Unfortunately, as its name implies, bioglass has poor mechanical properties, including high brittleness, low strength and low fracture toughness. Thus, 45S5 bioglass cannot be used for load-bearing bone repair applications. This drawback limits its use to very few clinical applications.

Recently, one of the promising materials identified for bone replacement has been calcium-silicate ($CaSiO_3$) due to its higher mechanical strength as compared to bioactive glasses. However, in comparison to 45S5 bioglass, $CaSiO_3$ ceramics have higher intrinsic solubility and produce higher concentrations of soluble factors in various media. In particular, pseudowollastonite (PsW) has a higher dissolution rate of soluble ionic factors as a result of its unstable "three-ring silicate" crystal structure, in comparison to the stable "chain-silicate" structure of wollastonite. Released Ca ions combine with $PO_4^{3-}$ ions present in blood or the in vitro test medium, and heterogeneously nucleate and grow as hydroxyapatite (HA, $Ca_{10}(PO_4)_6(OH)_2$) on $CaSiO_3$. Higher dissolution leads to faster bone-like apatite formation. This bone-like apatite layer facilitates implant-bone bonding (osteoconductivity) of the bioactive material. However, high Si concentrations, >120 ppm, released from a variety of silicate biomaterials are cytotoxic to osteoblasts, causing programmed cell death (apoptosis). The concentration of soluble factors released from calcium-silicate based material is a critical parameter defining whether the material will be osteoinductive or only osteoconductive, as well as whether it will be toxic in vivo. $CaSiO_3$ ceramics release high ion concentrations, whereas osteoinductivity of the material requires much lower concentrations of soluble factors. In order to activate osteoinductivity of $CaSiO_3$, the concentration of soluble factors released from sintered (HTS) $CaSiO_3$ needs to be decreased.

In vitro assessment of an implant's biocompatibility and osteoinductivity (osteoinductive potential) is typically performed by observing cell proliferation of bone cells and osteogenic differentiation of immature mesenchymal stem cells (hMSCs) in contact with the implant. In vitro cell studies on PsW reportedly demonstrated an increase in both the rate and total numbers of bone nodules formed. However, no improvement was detected in either cell proliferation or differentiation. It has also been reported that $CaSiO_3$ is superior to tricalcium phosphate (TCP) in cell attachment, proliferation, and differentiation. Further, fine-grained PsW showed less cell attachment and lower viability than a coarse-grained PsW surface. This was attributed to the higher Si ion dissolution (>120 ppm) from the fine grained PsW. As noted above, these high ion concentrations are cytotoxic. Cell growth and osteogenic differentiation of hMSCs has also been studied on two $CaSiO_3$ polymorphs, PsW ($\beta$-$CaSiO_3$) and wollastonite ($\alpha$-$CaSiO_3$). The PsW polymorph, which initially releases cytotoxic Si levels, is observed to be more osteoinductive than the wollastonite polymorph. However, the osteoinductivity of $CaSiO_3$-based ceramics versus 45S5 bioglass with regard to osteoblast cell proliferation and differentiation has not been previously reported.

It has now been discovered that LTS can be used on HTS-processed calcium silicate $CaSiO_3$ to increase the density of calcium silicate ceramics thereby improving microstructural and mechanical properties under relatively mild conditions. Thus, LTS via carbonation densifies HTS processed $CaSiO_3$ and significantly enhances the mechanical properties of $CaSiO_3$ ceramics in a cost-effective manner to achieve the mechanical properties of cortical bone comprising three steps:

(a) a porous ceramic compact having a network of interconnected pores is prepared,
  (b) the porous compact is then infiltrated with a fluid composed of reactive cations and/or anions,
  (c) a hydrothermal reaction causes part of the porous compact material to dissolve and react with the fluid to form a product that reactively grows while filling the pore space.

The LTS method produces core-shell structures including cores of partially carbonated acicular $CaSiO_3$ grains surrounded by $SiO_2$-rich layers that are in turn encapsulated by $CaCO_3$ particles. The reaction products $CaCO_3$ and $SiO_2$ are chemically more stable than $CaSiO_3$ and are biologically compatible. Moreover, $CaCO_3$- and $SiO_2$-rich amorphous phase reaction products encapsulate the highly soluble $CaSiO_3$ thereby addressing the drawback of an excessively high concentration of soluble factors being released from the $CaSiO_3$ ceramic. Thus, the LTS method is a promising way to control $CaSiO_3$ solubility since during LTS processing highly soluble $CaSiO_3$ is partially consumed and surrounded by less soluble reaction products during the carbonation reaction. In this way, the present carbonation process optimizes soluble ion concentrations released from $CaSiO_3$ ceramics.

Experimental Strategy

The effects of High Temperature Sintering (HTS) and Low Temperature Solidification (LTS) processes on dissolution behavior, in vitro cell proliferation, and osteogenic differentiation of $CaSiO_3$ materials were evaluated. First, $CaSiO_3$ compacts were processed by the HTS method. Thereafter the LTS carbonation process was used to densify $CaSiO_3$ green bodies and to further densify $CaSiO_3$ which has been pre-sintered. HTS-only $CaSiO_3$ samples were used as controls. As noted above, the term HLTS is employed to designate $CaSiO_3$ ceramics prepared by high temperature sintering followed by low temperature solidification, and the vales 1100, 1150, and 1200 associated with the HTS and HLTS terms represent sintering temperatures applied during sintering. Crystalline phase analysis and the degree of carbonation were monitored to characterize samples prior to evaluation of their dissolution and in vitro behavior. In order to evaluate dissolution behavior of these ceramics, $CaSiO_3$ compacts processed by HTS, LTS, and HLTS were immersed in Simulated Body Fluid (SBF) for different time periods. After SBF soaking, the concentration of Ca, Si and P ions, pH change of the SBF, and weight loss of samples were monitored. Thin-Film X-Ray Diffraction (TF-XRD) and Field Emission Scanning Electron Microscopy (FE-SEM) were used to probe for apatite formation resulting from SBF soaking. In vitro cell studies were performed to evaluate the composite's cytotoxicity, cell adhesion properties, and proliferation properties when presented with mouse osteoblast progenitor cells (MC3T3). After preliminary evaluation of $CaSiO_3$ samples using the cell proliferation test, the HTS1100 and H1100LTS samples were eliminated, and control 45S5 bioglass was included in the osteogenic differentiation test. The composite's osteogenic ability was evaluated using osteogenic differentiation of human mesenchymal stem cells (hMSCs).

Ion Dissolution and Apatite Formation of HTS, LTS, and HLTS $CaSiO_3$ Scaffolds

The XRD patterns of $CaSiO_3$ ceramics processed by HTS, LTS, and HLTS before and after soaking in SBF for 21 days showed the following. The characteristic peaks of carbonated apatite ($2\theta=25.7°$ and $2\theta=31.7°$) were detected on $CaSiO_3$ sintered at 1150 and 1200° C. (HTS1150, HTS1200), their corresponding carbonated forms (H1150LTS, H1200LTS), and on 45S5 bioglass control. Sintered and carbonated (HLTS) materials showed relatively low intensity apatite peaks compared to only sintered forms of $CaSiO_3$ (HTS-only). Observation of apatite peaks accompanied by significant reduction in the diffraction intensity of the original phases of the ceramics indicated apatite layer formation on the sample surface. The intensity of the apatite peaks increased with increasing sintering temperature of the HTS specimens. TF-XRD patterns of sample surfaces showed apatite nucleation as a function of SBF immersion period. The apatite formation on the sample surface appeared after (i) 1 day for 45S5 bioglass, (ii) 7 days for HTS1200 $CaSiO_3$, and (iii) 14 days for HTS11500 $CaSiO_3$. Thus, apatite formation on sintered-then-carbonated (HLTS) samples was delayed compared to their sintered-only (HTS-only) forms. In addition, the lower intensity of apatite peaks indicated that apatite formation is limited in carbonated materials compared to sintered-only $CaSiO_3$.

Figure 5:
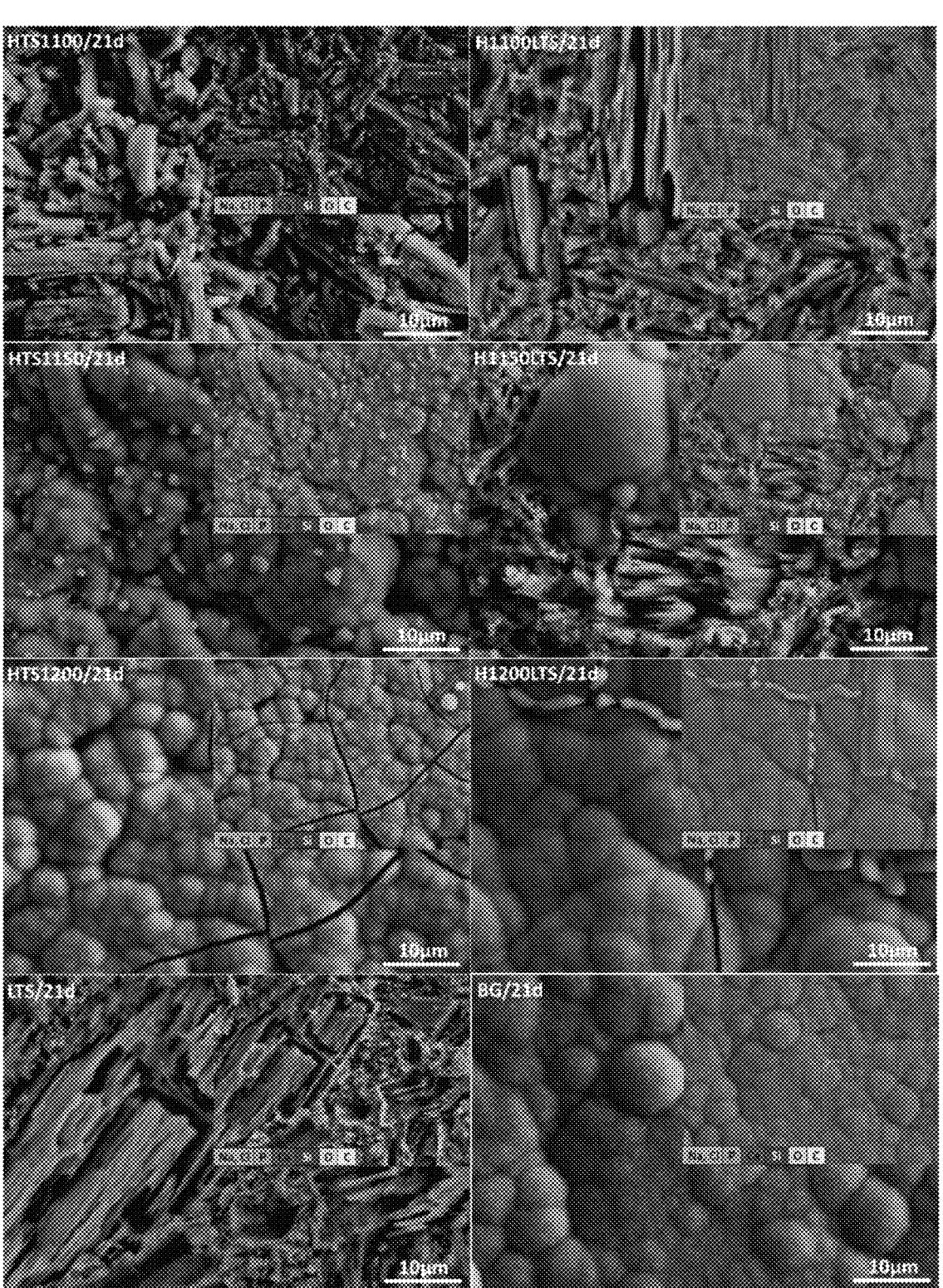
FIG. 5 shows SEM images of HTS, LTS or HLTS processed $CaSiO_3$ scaffolds after soaking in SBF for 21 days. Some NaCl precipitated from the SBF was detected in the EDS spectra.
Figure 6:
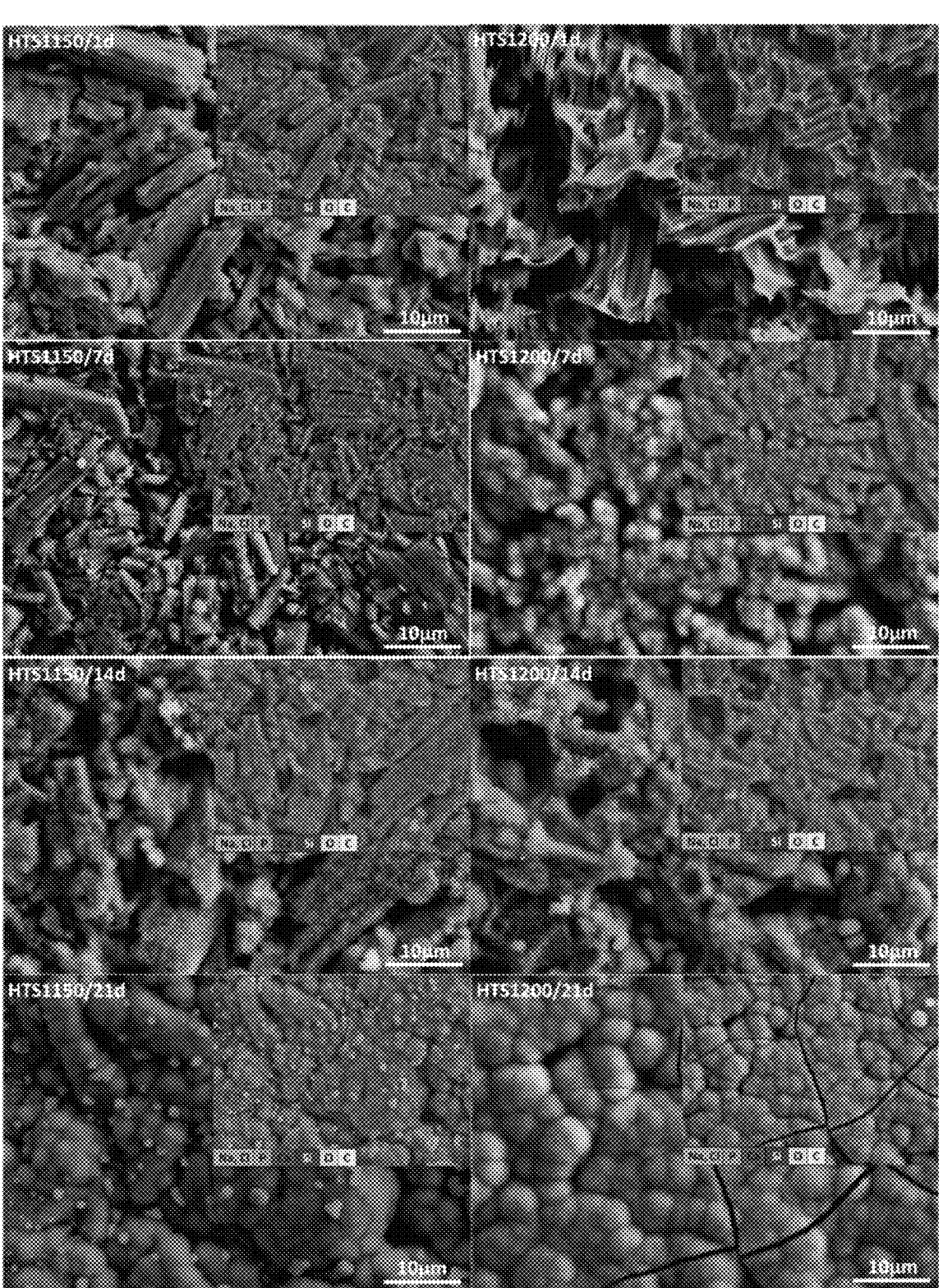
FIG. 6 shows SEM images of the surfaces of $CaSiO_3$ scaffolds sintered at 1150° C. (HTS1150) and 1200° C. (HTS1200) after soaking in SBF for 1, 7, 14 and 21 days. Some NaCl precipitated from the SBF was detected in the EDS spectra.
Figure 7:
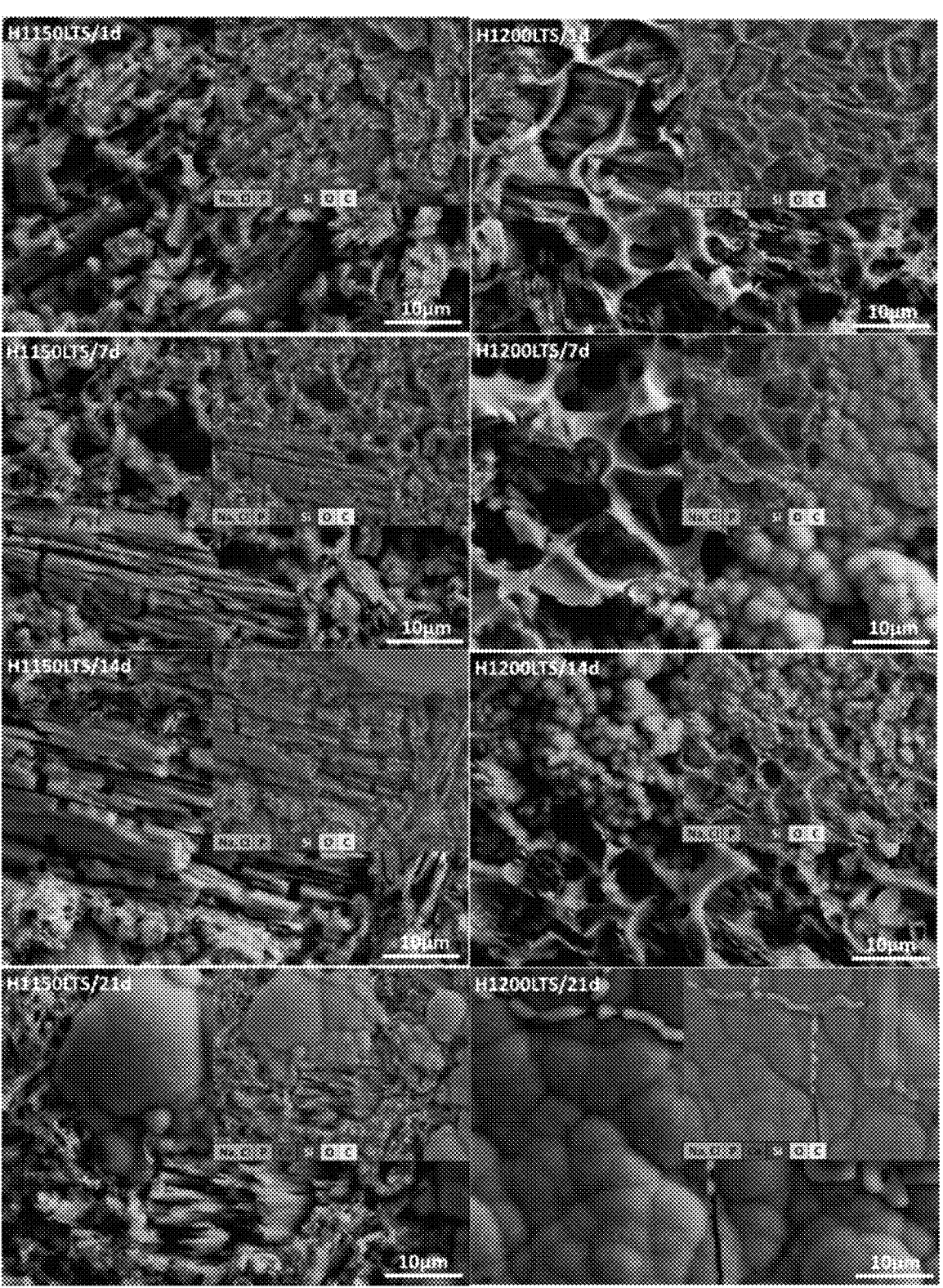
FIG. 7 shows SEM images of the surfaces of $CaSiO_3$ scaffolds carbonated after sintering at 1150° C. (H1150LTS) and 1200° C. (H1200LTS) after soaking in SBF for 1, 7, 14 and 21 days. Some NaCl precipitated from the SBF was detected in the EDS spectra.
Figure 8:
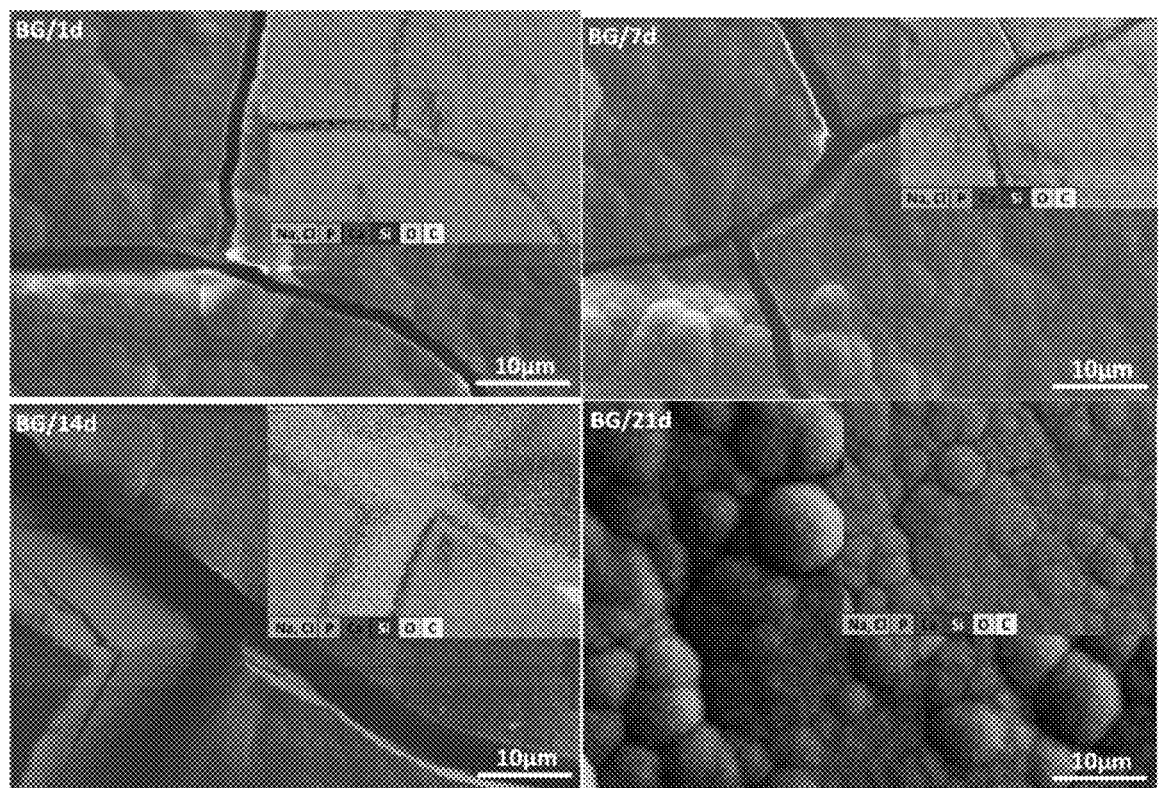
FIG. 8 shows SEM images of the surfaces of 45S5 bioglass scaffolds after soaking in SBF for 1, 7, 14 and 21 days.

SEM micrographs and EDS-microanalysis of the sample surfaces after immersion in SBF for 21 days (FIG. 5) showed apatite formation on HTS1150, HTS1200, H1150LTS, and H1200LTS $CaSiO_3$ and 45S5 bioglass surfaces, which confirmed XRD results. A continuous apatite layer with typical "cauliflower" morphology covering the entire surface of the sample was observed for HTS1150, HTS1200, H1200LTS, and the bioglass, whereas H1150LTS samples showed only incipient apatite formation that failed to entirely cover the sample surface. Apatite formation was not detected on (a) the reacted green $CaSiO_3$ (LTS), (b) low temperature sintered $CaSiO_3$ (HTS1100) and (c) low temperature sintered-then-reacted $CaSiO_3$ (H1100LTS) during the test period. SEM/EDS microanalysis showed that the newly formed apatite layer predominantly contained Ca, P and low levels of Si, with the atomic ratio of calcium to phosphorus being about 1.66 after 21 days of soaking. The EDS analysis of carbonated samples showed that $CaSiO_3$ preferentially dissolves in SBF while the carbonation products, the silica-rich phase and calcite, remained as an interconnected porous microstructure (FIG. 7). Preferential dissolution of $CaSiO_3$ can be observed more clearly on H1200LTS samples due to faster dissolution of PsW compared to the wollastonite phase in the H1150LTS samples. The morphological changes of apatite-forming surfaces after 1, 7, 14 and 21 days of immersion in SBF are shown in FIGS. 6, 7 and 8. Confirming the XRD results, the apatite layer formation appeared after (i) 1 day for 45S5 bioglass, (ii) 7 days for HTS1200 $CaSiO_3$, and (iii) 14 days for HTS11500 $CaSiO_3$. Both XRD and SEM analysis revealed that apatite formation on sintered and carbonated (HLTS) $CaSiO_3$ occurred more slowly and in more limited amounts compared to the only sintered (HTS-only) $CaSiO_3$.

Changes in soluble Ca and Si concentrations in the SBF solution after 21 days of immersion (soaking) are shown in the following table as a function of sintering temperature:

| | Ca | Si |
|---|---|---|
| HTS1100 | 220.62 | 77.09 |
| HTS1150 | 501.02 | 82.77 |
| HTS1200 | 558.92 | 85.6 |
| LTS | 126.5 | 39.75 |
| H1100LTS | 147.12 | 43.03 |
| H1150LTS | 347.72 | 68 |
| H1200LTS | 406.52 | 84.1 |
| 45S5 Bioglass | 126.32 | 30.04 |

With increasing sintering temperature, the concentration of Ca and Si species released from the samples increased. By dissolution of HTS $CaSiO_3$, Si concentrations increased from 77 to 85 ppm and Ca concentrations increased from 220 to 560 ppm, with increasing sintering temperature. The difference in dissolution behavior of wollastonite (slow and incongruent) versus PsW (faster and congruent) can be explained by the difference in their silicate anion structure. $CaSiO_3$ is composed of covalently bonded Si—O tetrahedral network formers and weakly bonded network-modifying Ca cations. While wollastonite is composed of silicate chains, PsW is composed of three-membered silicate rings. For wollastonite, weakly bonded network-modifying Ca cations are released into solution relatively faster, and hydrogen ions from the solution take their place. Covalently bonded network formers remain behind to form a hydrogen-enriched leached layer that dissolves more slowly. In addition, the hydrated silica in the leached layer undergoes reconstruction reactions, becoming more stable. In contrast, for PsW, once Ca ion leaves the structure, the three-membered silicate rings are not stabilized and release monosilicic acid into solution, resulting in higher ion concentrations than those released from PsW.

The changes in soluble Ca and Si concentrations in the SBF solution as a function of immersion time are as follows. The Ca and Si ion concentrations in SBF increased over the exposure time indicating partial dissolution of material. It has been reported that high Si concentrations (100-120 ppm), and Ca concentrations >400 ppm released from PsW are cytotoxic to osteoblasts. Ca and Si ionic concentrations released from carbonated samples decreased compared to their sintered-only forms. The Ca ion concentrations released from sintered and then carbonated (HLTS) $CaSiO_3$ in comparison to sintered-only (HTS-only) $CaSiO_3$ are (i) 147 ppm for H1100LTS vs. 220 ppm for HTS1100 (ii) 347 ppm for H1150LTS in comparison to 501 ppm for HTS1150, and (iii) 406 ppm for H1200LTS in comparison to ca. 560 μm for HTS1200. The Si ion concentrations released from HLTS samples in comparison to HTS-only samples are (i) 43 ppm for H1100LTS in comparison to 77 ppm for HTS1100, (ii) 68 mm for H1150LTS in comparison to 83 ppm for HTS1150, (iii) 84 ppm for H1200LTS in comparison to 86 ppm for HTS1200. The Ca and Si ion concentrations of carbonated samples decreased proportionally to their degree of carbonation.

Equilibrium solubility of Ca and Si ions from $CaSiO_3$ and the carbonation products, $CaCO_3$ and amorphous silica, in SBF were calculated by thermodynamic modelling. According to the model, the equilibrium solubility of $CaCO_3$ and amorphous silica are lower than that of $CaSiO_3$ although detailed analysis requires consideration of common ion effects. Thus, for carbonated samples, the interacting dissolution effects of all three phases, $CaSiO_3$, $CaCO_3$ and amorphous silica, in SBF medium must be considered.

The pH values of SBF solutions after sample infiltration and weight loss of samples in SBF as a function of immersion time revealed that, after a 1-day immersion, the pH increased from its original value of 7.4 to 8.1 for control 45S5 bioglass and to ca. 7.9 for all $CaSiO_3$ samples. The general trend for $CaSiO_3$ samples is increasing pH versus immersion time through 14 days, then constant pH for the remaining test time. During the dissolution of silicates, pH increase is expected due to acid consumption during cation/proton exchange. The pH increase became more gradual at longer soaking times due to slower dissolution of $CaSiO_3$ as the pH increases. The pH increased in proportion to the increase in Ca and Si ions released from the samples with increasing sintering temperatures. Sintered-then-carbonated (HLTS) samples showed a similar trend but the increase in pH was more gradual. The pH of 45S5 bioglass immersed in SBF, after a sharp increase to 8.1 at day 1, decreased to pH 8 and remained almost constant during the rest of the 21-day monitoring period. Changes in pH of the SBF solution followed a trend similar to the ion release profile. The pH increased with increasing ion release. According to the pH data, apatite formation was observed once the samples reached pH 8. Hence, LTS-only, HTS1100, and H1100LTS samples, having pH values lower than pH 8 showed no apatite formation. The pH of these samples showed a negligible increase or remained almost constant during the 21-day monitoring period. Similar to pH, weight loss of processed $CaSiO_3$ samples and control bioglass increased proportionately to the increase in Ca and Si ion release from the samples, which increased with both immersion time and increasing sintering temperature.

In Vitro Cell Studies on HTS, LTS, and HL TS $CaSiO_3$ Scaffolds

At 24 h of culture, cell (MC3T3) incubation with extracts of HTS-, LTS-, and HLTS-processed $CaSiO_3$ scaffolds showed no cytotoxicity effect of $CaSiO_3$. Cells showed significantly higher (p<0.05) adhesion to LTS $CaSiO_3$ and H100LTS $CaSiO_3$ samples compared to other $CaSiO_3$ samples, and similar to tissue culture plastic (TCPS) plates. Within the first 24 h of culture cell adhesion is known to be sensitive to morphology of the substrate. In addition, the chemistry of the substrate is important, particularly the availability of Ca ions, where released Ca concentrations of <240 ppm promote cell adhesion. Therefore, a high degree of dissolution from the surface, accompanied by a local pH increase could prevent cell adhesion over early immersion periods. Better cell adhesion is observed on the samples having a relatively low degree of dissolution. However, very low ion concentrations are not sufficient to stimulate osteoblast proliferation and osteogenic differentiation of cells.

Proliferation of MC3T3 on $CaSiO_3$ discs processed by HTS, LTS, and HLTS as well as on TCPS shows changes in the number of viable cells on the scaffolds after 1, 7, 14 and 20 days in the culture, which were quantitatively assessed. MC3T3 cultured on H1150LTS discs exhibited higher cell proliferation at each time point of the culture compared to those on the other discs, and the tissue culture plastic control. Statistical analysis of the 20-day proliferation data showed that proliferation on H1150LTS discs is significantly higher (p<0.05) compared to other $CaSiO_3$ samples. Viability on H1150LTS discs at days 7, 14 and 20 increased 4-, 10- and 11-fold, over day 1, respectively, indicating steady cell proliferation during the culture period.

In vitro osteogenic differentiation was assessed in terms of the alkaline phosphatase (ALP) activities of the hMSCs at 14 days. Osteoblastic differentiation of hMSCs on $CaSiO_3$ disc surfaces processed by HTS, LTS and HLTS in growth medium showed that ALP activity on H1150LTS discs was significantly greater than that on the other samples or 45S5 bioglass (used as control).

Thus, for HTS $CaSiO_3$ samples the concentrations of soluble factors in SBF increased markedly with increasing sintering temperature. The adhesion and proliferation of osteoblastic cells and osteogenic differentiation of hMSCs decreased with increasing concentrations of soluble factors. For LTS and HLTS $CaSiO_3$ samples, the concentrations of soluble factors released were found to decrease in proportion to the degree of carbonation. A significant increase in proliferation of osteoblastic cells and osteogenic differentiation of hMSCs for H1150LTS substrates indicated that the amount of the soluble factors released from H1150LTS samples, Si ion concentration of ca. 49 ppm and Ca ion concentration of ca. 237 ppm at 14-day SBF immersion, should be in an ideal range to activate stem cells for differentiation to osteoblast cells during culturing.

Thus, the experimental results support the hypothesis that the inventive carbonation process improves biocompatibility and osteoinductivity properties of HTS $CaSiO_3$ ceramics by limiting the high Ca and Si ion concentrations released from $CaSiO_3$, to achieve optimum ion concentrations for bone repair. When the carbonation process was used for green $CaSiO_3$ and sintered $CaSiO_3$ samples, soluble factor concentrations were found to decrease with increasing degree of carbonation. The partial consumption of highly soluble $CaSiO_3$ by carbonation leads to the formation of less soluble $CaCO_3$ and amorphous silica phases. These reaction products play an important role in decreasing the concentration of soluble factors released from the ceramic.

Cell proliferation and osteoinduction on ceramic substrates requires the release of an optimum concentration of soluble factors in order to encourage bone growth. Whereas high concentrations of soluble factors are toxic to cells, concentrations of Ca and Si ions that are too low fail to induce cell proliferation and osteoinductivity. Therefore, in order to have osteoinductive material the concentration of soluble factors released from sintered (HTS) $CaSiO_3$ needs to be balanced in order to reach optimum levels. As demonstrated herein, an appropriate degree of carbonation (LTS) leads to lower, and appropriate, ion concentrations being released from the $CaSiO_3$ composite, and the LTS carbonation process can be used to optimize soluble ion concentration release from the $CaSiO_3$ ceramic. Of the carbonated samples examined to date, only one release range of soluble factors, achieved by H1150LTS substrates, provided superior cell proliferation and osteogenic differentiation compared to all other samples.

Thus, the ceramic composite properties, including density, porosity, strength, and the ability to release an optimum concentration of soluble factors, can be controlled/tuned/adjusted by HTS and LTS process conditions, depending on the intended application.

According to thermodynamic modeling, the equilibrium solubility of Ca and Si ions from $CaSiO_3$ is much greater than the solubility limit of the Ca ions from $CaCO_3$ and the Si ions from amorphous silica. However, since $CaSiO_3$ is not fully consumed and converted to less the soluble $CaCO_3$ and amorphous silica during LTS densification, thermodynamically there should be no decrease in the solubility of the composite. Thus, if enough time is given, it is expected that carbonated substrates should reach similar Ca and Si ion equilibrium solubility levels as sintered-only $CaSiO_3$ substrates. Therefore, it can be concluded that the carbonation process has not altered the thermodynamic solubility of the material; instead, ion release is kinetically controlled.

Literature thermodynamic solubility values of $CaSiO_3$ and the carbonation products, $CaCO_3$ and amorphous silica, in water at 25° C., are assembled in the following table:

| Mineral | Solubility | |
| --- | --- | --- |
| | in H₂O at 25° C. (mol/l) | in SBF at 37° C. (g l⁻¹) HSC software |
| $CaSiO_3$ (Wollastonite) | | $1.9 \times 10^{-5}$ [1] |
| $CaSiO_3$ (PsW) | | $3.4 \times 10^{-5}$ [1] |
| $CaCO_3$ (Calcite) | $3.36 \times 10^{-9}$[2] $4.5 \times 10^{-9}$[3] | |
| $CaCO_3$ (Aragonite) | $6 \times 10^{-9}$[3] | |
| $SiO_2$ Amorphous Silica | 120 ppm [3] [4] 100 ppm [5] | |
| $Ca_{10}(PO_4)_6(OH)_2$ (Hydroxyapatite) | $3.7 \times 10^{-58}$ [6] | |

[1] M. A. Sainz, P. Pena, S. Serena, and A. Caballero, "Influence of design on bioactivity of novel CaSiO3—CaMg(SiO3)2 bioceramics: In vitro simulated body fluid test and thermodynamic simulation," *Acta Biomater.*, vol. 6, no. 7, pp. 2797-2807, 2010.
[2] Lide David R., "Solubility Product Constants," in *CRC Handbook of Chemistry and Physics*, 87th ed., David R. Lide, Ed. Taylor & Francis, 2006, pp. 118-120.
[3] K. B. Krauskopf, *Introduction to geochemistry*, 2nd edition. New York: McGraw-Hill., 1979.
[4] S. Sjöberg, "Silica in aqueous environments," *J. Non. Cryst. Solids*, vol. 196, pp. 51-57, 1996.
[5] G. B. Alexander, W. M. Heston, and R. K. Iler, "The Solubility of Amorphous Silica in Water," *J. Phys. Chem.*, vol. 58, no. 6, pp. 453-455, 1954.
[6] E. C. Moreno, T. M. Gregory, and W. E. Brown, "Preparation and solubility of hydroxyapatite," *J. Res. Natl. Bur. Stand. Sect. A Phys. Chem.*, vol. 72A, no. 6, p. 773, 1968.

However, there is a paucity of experimental equilibrium solubility limit data for $CaSiO_3$, $CaCO_3$ and the amorphous silica phases in SBF salt solution at pH 7.4 and temperature of 37° C. in the literature, indicating that thermodynamic solubility of the system may not have been evaluated thoroughly. Therefore, equilibrium solubility of Ca and Si ions from $CaSiO_3$, $CaCO_3$, amorphous silica and HA were predicted using thermodynamic modeling to evaluate the system thermodynamically. According to the model, Ca ion concentrations released from sintered $CaSiO_3$ (HTS1150 and HTS1200) samples reach the equilibrium solubility limit of $CaSiO_3$. However, Ca ion concentrations released from carbonated samples do not reach the equilibrium solubility level of $CaSiO_3$ during the test period. Therefore, it can be concluded that the Ca dissolution from carbonated samples should be kinetically limited. The same trend was expected for Si ions released from sintered and carbonated samples; however, the modeling indicated very low Si solubility levels from $CaSiO_3$ and amorphous silica, which conflicts with the present experimental data as well as with available literature.

HA formation following the ion dissolution in SBF can be thermodynamically evaluated based on the equilibrium solubility limits obtained from the model. The concentration of Ca ions released from processed $CaSiO_3$ are above the equilibrium solubility limit of calcite and HA. Therefore, since the saturation limit is exceeded for $CaCO_3$ and HA, these phases can thermodynamically form. Formation of HA is more favorable, due to a lower standard energy of formation for HA, $\Delta H_f^o = -3,212$ kcal/mole, compared to $CaCO_3$, with a $\Delta H_f^o = -289$ kcal/mole. HA formation could be observed on the surfaces of HTS1150 and HTS1200 samples, while no HA was observed on HTS1100. HA formation on HTS1100 samples might be kinetically limited due to lower concentrations of soluble ions eluting from HTS1100. Therefore, if sufficient immersion time is given, HA formation would be expected on this sample as well. Following the carbonation process, even though there is a reduction in the ion concentrations, the Ca ion concentrations released from $CaSiO_3$ and $CaCO_3$ exceeded the equilibrium solubility of HA. Hence, HA formation on surfaces of the carbonated samples is expected; however, it may proceed more slowly due to lower ion concentrations versus sintered-only $CaSiO_3$.

Without wishing to be bound by any particular theory, it is believed that a decrease in Ca and Si ion concentrations following the carbonation process is due to dissolution of ions from the composite being kinetically limited. Assuming that the dissolution of soluble ions from carbonated samples is kinetically limited, kinetic factors that might be effective to achieve lower ion concentrations of soluble factors following the carbonation process include relative quantity of the phases, microstructure, surface area and pH. These are parameters that can be manipulated to affect dissolution kinetics so as to result in beneficial concentrations of soluble factors from H1150LTS ceramics.

The relative quantities of highly soluble $CaSiO_3$ and the lower solubility reaction products, $CaCO_3$ and amorphous silica, can affect dissolution kinetics. The relative quantities of reaction products in the $CaSiO_3$ matrix were quite different depending on the level of sintering which in turn affected the degree of subsequent carbonation. Depending on relative quantities of highly soluble $CaSiO_3$ or less soluble $CaCO_3$ and amorphous silica in the composite, the ionic concentrations of soluble factors observed in the SBF varies. Considering that the degree of carbonation is not dependent on the phase of the $CaSiO_3$, (wollastonite vs. PsW show no difference in reactivity during carbonation), the observed decrease in degree of carbonation with increasing sintering temperature apparently is due to coarsening of the morphology and 85% reduction in the surface area. For H1200LTS samples, the decreased degree of carbonation provides more calcium silicate enabling greater levels of soluble ionic factors to appear in the solution. In contrast, H1100LTS samples sintered at the lowest temperature show a very high degree of carbonation; therefore, the lower amount of accessible $CaSiO_3$ in these samples resulted in a very low concentration of soluble factors compared with the other carbonated samples. However, H1150LTS having an intermediate level of $CaSiO_3$ resulted in release of an intermediate concentration of soluble factors.

Microstructure appears to be an important parameter affecting dissolution kinetics of the carbonated samples. The reaction products surrounding the $CaSiO_3$ matrix act as a barrier slowing down the dissolution of $CaSiO_3$. For the lowest temperature sintered material prior to carbonation (H1100LTS), the microstructure is comprised of an array of discrete fine $CaSiO_3$ crystals that are highly reactive during the carbonation step and thus generate a protective carbonate/amorphous silica reaction layer around discrete particles. Soluble factor release in SBF is thus highly reduced for H1100LTS. On the other hand, the highest temperature sintered-then-carbonated material (H1200LTS) exhibits a much coarser interconnected network-like structure of $CaSiO_3$ that is less reactive under the carbonation conditions. Yet, this less carbonated material still has enough $CaSiO_3$ to release high quantities of soluble factors. As identified herein the intermediate-sintered-then-carbonated material (H1150LTS) optimizes the solubility and release of ions. The fine $CaSiO_3$ particles sinter to form a network-like structure that is sufficiently fine-structured to produce moderate reactivity during carbonation, so that carbonation provides a structure that partially protects the $CaSiO_3$ from SBF to release a biologically favorable level of soluble ionic factors.

Surface area appears to be another parameter affecting the dissolution kinetics of carbonated samples. Substrates having higher surface area should a yield higher concentration of soluble factors. Before carbonation, the surface area of $CaSiO_3$ decreased by 85% with increasing sintering temperature. In contrast, the concentration of soluble ions increased with increasing sintering temperature due to faster dissolution of ions from the PsW phase. Therefore, it can be concluded that microstructural change of the $CaSiO_3$ affects dissolution kinetics of $CaSiO_3$ much more strongly compared to surface area change. For the carbonation reaction, the final surface area of carbonated samples increased versus surface area of the highly soluble $CaSiO_3$ compacts prior to carbonation. This increase in surface area is proportional to the degree of carbonation and formation of the reaction products $CaCO_3$ and amorphous silica in the leached layer. Due to a balancing increase in surface area arising from formation of these less soluble phases, there is no apparent contribution to the concentration of soluble factors released (dissolution kinetics).

Interacting dissolution appeared to be a parameter affecting ion concentrations of carbonated samples. The mineral-fluid interface of silicate minerals is complex and still not fully understood. With regard to the present disclosure, involvement of $CaCO_3$ and silica-rich amorphous phases in addition to $CaSiO_3$, and the use of a SBF salt solution versus pure water brings more complexity. Even though the ion concentration data is not sufficient to explain the interacting dissolution effects of all three phases in SBF medium, without wishing to be bound by any particular theory, it is believed that dissolution behavior based on individual dissolution characteristics of each phase depends on pH.

The kinetics of dissolution change based on the pH of the solution. For sintered-only samples, $CaSiO_3$ is the only compound available for ion dissolution and release. The alkaline earth silicate mineral wollastonite dissolves faster in acidic solution than neutral solution. $CaSiO_3$ dissolution increases the pH due to acid consumption (capture of $H^+$ ions). Partial dissolution of $CaSiO_3$ in SBF is shown by the following equation:

$$CaSiO_{3\ (s)} + 3H_2O_{(l)} \leftrightarrow Ca^{2+}_{(aq)} + 2OH^- + H_4SiO_{4(aq)}$$

Monosilicic acid, $H_4SiO_4$, is the predominant form of Si in solution up to pH 9. The literature reports that $CaSiO_3$ dissolves incongruently due to preferential release of Ca ions from the $CaSiO_3$ surface and concomitant formation of silica-rich leached layers at pH values lower than 8.5. Si—OH groups on the surface form by the exchange of Ca ions with hydrogen ions ($H^+$) from the solution.

During carbonation, $CaSiO_3$ is partially consumed and replaced by the less soluble reaction products $CaCO_3$ and amorphous silica. The decrease in the amount of solvent-accessible $CaSiO_3$ in samples results in a decrease in the concentration of soluble factors released from the densified samples, together with a gradual increase in pH. Since $CaCO_3$ is an alkaline mineral it dissolves more slowly at the weakly alkaline pH of SBF, the alkalinity being produced by the above-described Ca-hydrogen ion exchange. $CaCO_3$ dissolution also consumes $H^+$ leading to a further increase in the pH. However, since $CaCO_3$ is less soluble than $CaSiO_3$, only a limited increase in the pH is expected. The carbonate dissolution reaction is shown below:

$$CaCO_{3(s)} + H_2O_{(l)} \leftrightarrow Ca^{2+}_{(aq)} + OH^- + HCO_3^-$$

Amorphous silica has limited solubility in the pH range 2-9. Similar to the dissolution process of silicates, dissolution of silica is based on hydrolysis of Si—O—Si bonds. The negatively charged silica surfaces protonate and dissociate to release monosilicic acid ($H_4SiO_4$):

$$SiO_{2(s)} + 2H_2O_{(l)} \leftrightarrow H_4SiO_{4(aq)}$$

The solubility of amorphous silica is reported to be pH-independent in acidic and weakly alkaline solutions up to pH 9. The solubility of silica increases dramatically at pH values over 9. However, the pH of the SBF solution described above does not reach this high solubility generating limit. Considering that the pH of the SBF solution ranges from 7.4 to 8.5, the dissolution rate of $CaSiO_3$, $CaCO_3$ and amorphous silica are all expected to be low.

Without wishing to be bound by any particular theory, based on the behavior of each individual phase a possible mechanism involving the interaction of $CaSiO_3$, $CaCO_3$, and amorphous silica phases with SBF solution is envisioned to encompass at least the following:

(i) $Ca^{2+}$ ions are released from $CaSiO_3$ and, to a limited degree, from $CaCO_3$, increasing the pH;

(ii) Hydrolysis at the surface of the densification product, amorphous silica, and the Si—OH surfaces of $CaSiO_3$, releases $H_4SiO_4$ into the SBF solution (see equations immediately above);

(iii) Partial condensation of $\equiv Si$—OH groups at the surface occurs in the layers depleted of Ca ions:

$$\equiv Si—OH + HO—Si \equiv \rightarrow \equiv Si—O—Si \equiv + H_2O;$$

(iv) Once the released $Ca^{2+}$ and $OH^-$ ions exceed the solubility of apatite in SBF, apatite nucleation and crystallization occur on favorable silica-rich surfaces:

$$10Ca^{2+}_{(aq)} + 6HPO^{2-}_{4(aq)} + 8OH^-_{(aq)} \leftrightarrow Ca_{10}(PO_4)_6(OH)_{2(s)} + 6H_2O.$$

Surface chemistry appears to be another parameter affecting dissolution kinetics of carbonated samples. Surface charges of sintered and carbonated $CaSiO_3$ under SBF test conditions were predicted based on point of zero charge (PZC; the pH at which solid surface charges are zero) for each phase. Under acidic conditions, for pH values below the pHPzc, the mineral surface becomes more positive and the solution becomes more alkaline. Under alkaline conditions, for pH values above this pHPzc, the mineral surface becomes less positive and the solution becomes more acidic. For sintered-only samples, $CaSiO_3$ is the sole material phase present. The PZC of wollastonite is reported to be ca. pH 7. Thus, the surface of $CaSiO_3$ in a pH range of 7.4 to 8.5 could be somewhat negatively charged but should be predominantly uncharged (zero charge). For carbonated (densified) samples, in addition to $CaSiO_3$, surface chemistry of calcite and amorphous silica should also be considered. The PZC of calcite is reported to be ca. pH 8-9. Thus, the surface of $CaCO_3$ could be somewhat positively charged but should be close to zero. The PZC for amorphous silica is reported to be ca. pH 3.5. Thus, the surface of amorphous silica should be negatively charged. For carbonated samples, net surface charge of the composite might be negative due to the high negative charge on amorphous silica and negligible amount of charging of other phases. As a result, the SBF solution tends to become more acidic. The pH of carbonated samples, in comparison to sintered-only $CaSiO_3$, is relatively lower. It is believed that a decrease in the amount of dissolved $CaSiO_3$ is the main reason for the limited increase in pH. In addition, surface charges contribute to lower pH values. However, the effect of surface charges is considered to be limited due to the low surface area of the material (maximum ca. 2 m²/g). Thus, surface charges should not induce a major change in the solution pH.

Considering these possible kinetic factors, it is believed that the carbonation process kinetically limits the dissolution of Ca and Si ions from the $CaSiO_3$-based composite.

The H1150LTS samples, having exceptional biocompatibility and osteoinductivity properties, can expedite the healing process to repair bone defects. In addition to the biochemical compatibility and osteoinductivity requirements, biomechanical compatibility of the implant with natural bone is an important parameter for successful bone implants. As noted above, carbonation of (a) green $CaSiO_3$ (LTS-only), (b) $CaSiO_3$ sintered at 1100 (H1100LTS), and (c) $CaSiO_3$ sintered at 11500 (H11500LTS) similarly enhanced densification, and mechanical strength and toughness compared to the sintered-only (HTS-only) $CaSiO_3$. Due to the relatively lower degree of carbonation of sintered-then-carbonated (HLTS) $CaSiO_3$ samples compared to those of carbonated green (LTS-only) $CaSiO_3$, it is expected that HLTS samples will have lower densification and a lower degree of enhancement in mechanical properties compared to LTS-only $CaSiO_3$. However, the high temperature sintering process (especially at sintering temperatures of about 1150° C.) and formation of a lower density phase of $CaSiO_3$ (vaterite taking the place of aragonite) contributed to achieving similar densification and mechanical properties of HLTS $CaSiO_3$ scaffolds. By applying the carbonation process, the compressive strength of the HLTS scaffolds reached 279 MPa, flexural strength increased to 65.5 MPa and toughness rose to 1.87 MPa·m$^{1/2}$ which is close to these same parameters for cortical bone, and about twice that of conventionally sintered $CaSiO_3$. LTS-only, H1100LTS and H1150LTS samples all provide similarly promising mechanical properties; however, only H1150LTS optimizes biomechanical and biochemical compatibility, as well as osteoinductivity. This demonstrates that H1150LTS samples produced by carbonation of sintered $CaSiO_3$ at 1150° C. meet the essential conditions for osteoinductive bone implants by providing the right concentration of released soluble factors and achieving greater cell proliferation and osteogenic differentiation in addition to having appropriate mechanical properties. H1150LTS $CaSiO_3$ having improved mechanical properties, biocompatibility, and superior osteoinductivity, thus becomes a potential candidate for use as bioactive bone implants.

In summary, the present in vitro cell results revealed that concentrations of soluble factors significantly influenced osteoinductivity. Applying the LTS carbonation process to pre-sintered $CaSiO_3$ addresses the drawback of excessively high ion dissolution from sintered $CaSiO_3$ by reducing the concentration of soluble factors from toxic levels. Significantly greater proliferation of MC3T3 cells on H1150LTS compared to other $CaSiO_3$ substrates and significantly greater osteogenic differentiation of hMSCs on H1150LTS compared to other $CaSiO_3$ substrates or osteoinductive 45S5 bioglass control, indicated that the ionic soluble factors of H1150LTS scaffolds are released in an optimal concentration range for enhancing biocompatibility and osteoinductivity. In vitro cell proliferation and osteogenic differentiation tests can identify promising concentrations of soluble factors, for example, a Si ion concentration of ca. 49 ppm and a Ca ion concentration of ca. 237 ppm at 14-day SBF immersion. When released from H1150LTS $CaSiO_3$ these levels of soluble ionic factors stimulate cell activation for bone generation.

One aspect of the invention is directed to a composite material comprising a porous, carbonated, calcium silicate ceramic having a microstructure comprising interconnected open pores; where the calcium silicate surface defining the pores is partially or completely coated with an amorphous silica layer, and the silica coating comprises an overlayer of calcium carbonate crystals; where the silica coating and the calcium carbonate overlayer form a network that interconnects throughout the ceramic microstructure, but do not completely occlude the pores.

Another aspect of the invention is directed to a composite material comprising a porous, carbonated, calcium silicate ceramic having a microstructure comprising interconnected open pores; where the calcium silicate surface defining the pores is partially or completely coated with an amorphous silica layer, and the silica coating comprises an overlayer of calcium carbonate crystals; where the silica coating and the calcium carbonate overlayer form a network that interconnects throughout the ceramic microstructure, but do not completely occlude the pores, where the composite material is produced by i) providing a $CaSiO_3$ ceramic compact having a microstructure comprising interconnected open pores around ceramic grain boundaries; and ii) subjecting the compact to hydrothermal carbonation under Low Temperature Solidification (LTS) conditions comprising heating at <100° C. under about 10 to about 30 psig $CO_2$ gas, until the relative density increases by about 16% to about 20%. The relative density increase can be about 16%, about 17%, about 18%, about 19%, about 20%, or any value therebetween. In some embodiments the $CaSiO_3$ ceramic compact is sintered at a temperature between about 1100° C. and about 1200° C. and cooled before subjecting to LTS conditions. In other embodiments the $CaSiO_3$ ceramic compact is sintered at about 1150° C. The sintering temperature of the $CaSiO_3$ ceramic compact can be about 1100 or about 1125 or about 1150 or about 1175 or about 1200° C., or any value therebetween.

The $CaSiO_3$ compact of the composite material has a microstructure of inter-connected open pores that are enlarged by sintering at a temperature between about 1100° C. and about 1200° C., or any temperature therebetween. Preferably, the inter-connected open pores are enlarged by sintering at a temperature of about 1150° C.

The LTS conditions heat at a temperature of about 50° C. to <100° C. under about 15 to about 25 psig $CO_2$ gas. The LTS heating temperature can be about 50 or about 60 or about 70 or about 80 or about 90, up to <100° C. The LTS pressure of $CO_2$ gas can be about 15 or about 17 or about 19 or about 21 or about 23 or about 25 psig. In some embodiments the LTS conditions comprise heating at about 90° C. in about 20 psig $CO_2$ gas.

The inventive composite material can be in the form of a scaffold, or any other shape suitable for implantation in vivo. The composite material can have an amorphous silica layer that further comprises a calcium gradient. The compact of the composite material can be have any shape with dimensions to fit and fill a bone defect, either prior to, or after, sintering at about 1100° C. to about 1200° C.

A further aspect of the invention is directed to a method of forming a composite material, comprising the steps of: 1) providing a compact of a $CaSiO_3$ ceramic material having a microstructure comprising interconnected open pores; and 2) subjecting the compact to hydrothermal carbonation under Low Temperature Solidification (LTS) conditions comprising heating at <100° in about 10 to about 30 psig $CO_2$ gas C, until the relative density value increases by about 16% to about 20% to produce a carbonated ceramic material. The relative density increase can be about 16%, about 17%, about 18%, about 19%, about 20%, or any value therebetween. In some embodiments the $CaSiO_3$ ceramic compact is sintered at a temperature between about 1100° C. and about 1200° C. and cooled before subjecting to LTS conditions. In other embodiments the $CaSiO_3$ ceramic compact is sintered at about 1150° C. The sintering temperature of the $CaSiO_3$ ceramic compact can be about 1100 or about 1125 or about 1150 or about 1175 or about 1200° C., or any value therebetween. In some embodiments the $CaSiO_3$ ceramic compact is sintered at a temperature between about 1100° C. and about 1200° C. and cooled before subjecting to LTS conditions. The sintering temperature of the $CaSiO_3$ ceramic compact can be about 1100 or about 1125 or about 1150 or about 1175 or about 1200° C., or any value therebetween. In some embodiments the $CaSiO_3$ ceramic compact is sintered at about 1150° C.

Prior to the LTS hydrothermal carbonation step, the compact is pre-sintered at a temperature between about 1100 and 1200° C., or any temperature therebetween, to produce a continuous calcium silicate network compromising calcium silicate grains and grain boundaries in a continuous pore network, and to enlarge the interconnected open pores. Preferably the pre-sintering temperature is about 1150° C.

In the method as described above, the interconnected pores can have an average pore size between about 0.5 μm and about 3 μm. The average pore size can be about 0.5 or 0.7 or 0.9 or 1.1 or 1.3 or 1.5 or 1.7 or 1.9 or 2.1 or 2.3 or 2.5 or 2.7 or 2.9 or about 3 μm. The LTS conditions of the method comprise heating at a temperature of about 50° C. to <100° C. in about 15 to about 25 psig of $CO_2$ gas. The LTS heating temperature can be about 50 or about 60 or about 70 or about 80 or about 90, up to <100° C. The LTS pressure of $CO_2$ gas can be about 15 or about 17 or about 19 or about 21 or about 23 or about 25 psig. Preferably, the LTS conditions of the method comprise heating at a temperature of about 90° C. in about 20 psig of $CO_2$ gas.

The composite material formed by the above method preferably has any shape with dimensions suitable to fit and fill a bone defect, either prior to, or after, sintering at about 1100° C. to about 1200° C.

Yet another aspect of the invention is directed to a method of repairing a bone defect caused by trauma, infection or removal of a tumor, where the method comprises filling the bone defect with the composite material described above.

In summary:

The present invention provides bioactive ceramics with high osteoinductivity and osteoconductivity as well as mechanical properties similar to natural bone.

The present invention provides a ceramic composite implant free of organic osteoinductive agents (DMB, bone morphogenetic proteins possess, etc.) which possess osteoinductivity.

The present invention provides novel ceramic composite compositions and structures which are free of organic osteoinductive agents and which nevertheless induce osteoinductivity (osteogenic differentiation) when seeded with Human mesenchymal stem cells (hMSCs).

The present invention provides a osteoinductive ceramic composite (without any organic osteoinductive agent) that has excellent bioactivity comparable to existing osteoinductive bioglass, glass-ceramics and ceramics, biomechanical compatibili-ty with natural bone, and that can be produced through a combination of high temperature sintering and hydrothermal process of calcium silicate ceramics.

The present disclosure relates to novel bioactive ceramic compositions and structures as well as a process for preparing such ceramic composite compositions and structures.

The present disclosure relates to inorganic osteoinductive bone graft materials and a method for their preparation.

The present disclosure relates to methods for producing osteoinductive ceramic composites, in which a layer of less soluble ceramic is adhered to the surface of a highly soluble core.

Calcium silicate-based ceramic composites produced by carbonation of sintered calcium silicates meet the essential conditions to repair bone defects by having the optimal concentration of releasable soluble ionic factors that induce greater cell proliferation and osteogenic differentiation. These composites also have superior mechanical properties in comparison to sintered $CaSiO_3$ and 45S5 bioglass.

The microstructures produced by applying the HLTS process to calcium silicate ceramics provide controlled release of the soluble ionic factors.

The microstructures produced by applying the LTS process to HTS sintered calcium silicate bulk ceramics provide a controlled amount of Ca and Si ion release from the composite. Less soluble reaction products, $CaCO_3$ phases and an amorphous $SiO_2$-rich layer surround the calcium silicate core.

The structure produced by carbonation of sintered calcium silicate at 1150° C. provides a calcium silicate ceramic having a microstructure having interconnected open pores that are at least partially filled with a silica-rich first layer and a calcium carbonate-rich second layer at least partially covering the first layer. This structure provides controlled release of ions producing enhanced cell proliferation and osteogenic differentiation.

For the disclosed ceramic composite produced by HTLS, the first and/or second layer may completely or partially cover the core and/or first layer depending on the calcium silicate precursor(s) and the HLTS (HTS and LTS) process conditions, but are not limited to only these parameters.

A conventional high temperature sintering (HTS) process is conducted on green compacts to produce structures having a continuous calcium silicate network of calcium silicate grains with grain boundaries and interconnected open pores.

The HTS process produces a continuous calcium silicate network of calcium silicate grains and grain boundaries and a continuous pore network.

The HTS process is effective to control pore size and surface area of the calcium silicate core, while the LTS process controls the reaction percentage and the structure of the reaction products.

The HTS process is one controlling parameter in achieving controlled ion release to activate osteoblast production.

The LTS process is another controlling parameter in achieving controlled ion release to activate osteoblast production.

The composite material produced by the HLTS processes has a calcium silicate core wherein calcium silicate grains are bonded via grain boundaries forming a three-dimensional rigid network.

For the disclosed ceramic composite, the core, the first layer and the second layer may exist in a crystalline phase, an amorphous phase, or a combination thereof.

The ceramic composite composition can be prepared from pure raw (precursor) materials or by including other inorganic additive(s).

The ceramic composites can be prepared from precursor materials including, but not limited to, calcium silicate minerals or synthesized calcium silicates, and/or their combinations.

The ceramic composite can be prepared from a calcium silicate precursor which is crystalline, a mineral, synthesized, amorphous, or combinations thereof.

The ceramic composite composition can be prepared as a dense or as a highly porous structure.

The HLTS processes provide controlled porosity and pore size distribution of the microstructure. In addition, the initial composition can be mixed with a pore former to provide extended porosity and pore size distribution prior to sintering.

The ceramic composite composition can be prepared in any size and morphology (i.e., shape) depending on the intended application.

The osteoinductive property of the composite is independent from the presence of any organic osteoinductive agents. However, the composition can be combined with one or more organic osteoinductive agents depending on the intended application.

The osteoinductive property of the composite is independent of presence of any therapeutic agents. However, the composition can be combined with one or more therapeutic agents depending on the intended application.

The ceramic composite can be used to produce the implantable devices alone or in combination with other bone implant materials, for example as coatings and/or matrix materials for bone tissue repair and regeneration. Examples of devices include prosthetic implants, sutures, stents, screws, plates, tubes, and the like.

The ceramic composite can be used to produce implantable devices alone or in combination with autogeneic, allogeneic and xenogeneic implants, for example as coatings or matrix materials for bone tissue repair and regeneration. Examples of devices include prosthetic implants, sutures, stents, screws, plates, tubes and the like.

Biological response is dependent on the concentration of released ions from the composite material. The concentration of released ions from the ceramic composite can be controlled by selection of the chemical and physical properties of the calcium silicate precursor resource, pellet production method, conditions, and the degree of high temperature sintering in the HTS and LTS processes, but it is not limited to only these parameters.

As a major advancement compared to 45S5 bioglass materials, calcium silicate-based ceramic composites of the present invention possess mechanical properties comparable with native bone, making them suitable for load bearing applications.

The mechanical properties of the ceramic composites, among other variables, depend on volume fraction, grain size, crystal phase and shape of the crystals.

The level of bioactivity of the inventive ceramic composite depends on their composition and structure.

The present invention discloses a method for producing osteoinductive calcium silicate ceramic material by applying hydrothermal processes to high temperature sintered calcium silicate ceramics.

The ceramic composite properties, including density, porosity, strength, and ability to release an optimum concentration of soluble factors, can be controlled/tuned/adjusted by HTS and LTS process conditions, depending on intended application.

NON-LIMITING WORKING EXAMPLES

Example 1. Raw Material and Preparation of CaSiO₃ Compacts

Mineral based wollastonite (NYAD® 400, NYCO Minerals Inc, Willsboro, NY) with an average particle size of ca. 9 μm was used as the $CaSiO_3$ source. The average particle size was determined by a laser particle size analyzer (Zetasizer, Nano ZS, Malvern Instruments Ltd., Malvern, Worcestershire, UK). Industrial grade $CO_2$ (AirGas Inc., Piscataway, NJ) was used for the carbonation process. Water was filtered through a Progard® 2 and Q-guard® 1 purification system (EMD Millipore, MA) prior to use. The powder compacts of ca. 13 mm of diameter and ca. 13 mm of length were prepared by dry pressing using Automatic Carver Press (Model 4532, Wabash, IN) under 148 MPa. The compacts were then dried overnight in the drying oven at 90° C.

Example 2. High Temperature Sintering (HTS)

Powder compacts were sintered in a box furnace (CM Furnaces Inc., Rapid Temp Furnace, Bloomfield, NJ) at 1100° C., 1150° C., or 1200° C. respectively for 2 h, with heating rate of 2° C./min and cooling rate of 10° C./min.

Example 3. Low Temperature Solidification (LTS) on Green and Sintered CaSiO₃ Compacts The green and sintered ceramic compacts were reacted at 90° C. with 20 psig $CO_2$ gas input in a pressure steamer (All American #75×, Wisconsin Aluminum Foundry Co., Manitowoc, WI) for a minimum of 19 h. After the reaction, the samples were dried at 90° C. for 24 h.

Example 4. Characterization

Example 4A

X-ray diffraction (XRD) analysis was performed using a Bruker D8 Discover (Bruker AXS Inc., Madison, WI) with CuKα radiation (k=1.514 Å), parallel beam in the range 10-80° (2θ) with a 0.0180 step size and 0.5-s dwell time. PDF numbers of 97-020-1537 (wollastonite 1A-$CaSiO_3$), 97-008-7716 (pseudowollastonite (high temperature phase of $CaSiO_3$)), 97-028-0991 (aragonite-$CaCO_3$), 97-001-6710 (calcite-$CaCO_3$), 97-001-5879 (vaterite-$CaCO_3$), and 98-0039830 ($SiO_2$) published by the International Centre for Diffraction Data (ICDD, Newtown Square, PA) was used to identify the phases. Quantitative phase analysis of XRD profiles was refined by Rietveld method using MDI Jade 9 (Materials Data Inc., Livermore, California, USA).

Example 4B

Thermal gravimetric analysis (TGA) was performed on TA Q500 (TA Instruments, New Castle, DE) by heating from room temperature to 1000° C. at a rate of 10° C./min under nitrogen atmosphere at a flow rate of 100 ml/min. Weight loss in range of 200-800° C. corresponds to weight percentage (wt %) of $CO_2$ released as a result of carbonate decomposition as shown by the following equation:

$$CaCO_{3(s)} = CaO_{(s)} + CO_{2(g)}\uparrow$$

The weight percentage of $CO_2$ ($m_{CO2}$%) is proportional to the degree of carbonation (X TGA (%)) as shown in the following equation:

$$\lambda_{TGA}(\text{mol }\%) = \left(m_{CO_2}\%\right) \times \left(\frac{M_{CaSiO_3}}{M_{CO_2}}\right)$$

$$\lambda_{TGA}(\text{mol }\%) = \left(1 - \left(\frac{(m_i - m_{CO2})}{(m_i)}\right)\right) \times \left(\frac{M_{CaSiO_3}}{M_{CO_2}}\right)$$

$m_i$=initial sample mass in grams $m_{CO_2}$=mass of $CO_2$ in grans released from sample $M_{CaSiO_3}$=molecular weight of $CaSiO_3$, 116.16 g/mole $M_{CO_2}$=molecular weight of $CO_2$, 0.44.01 g/mole The net weight gain after carbonation process corresponded to the $CO_2$ intake during the carbonation reaction. The mass gain of each sample set was recorded after carbonation. The degree of carbonation ($\lambda_w$ (%)) was calculated from net weight gain as follows:

$$\lambda_w(\text{mol }\%) = \frac{(m_f - m_i) \times \left(M_{CaSiO_3}\right)}{(m_i) \times \left(M_{CO_2}\right)} \times 100$$

$m_i$ = initial sample mass in grams $m_f$ = final sample mass in grams (after carbonation)

$M_{CaSiO_3}$ = molecular weight of $CaSiO_3$, 116.16 g/mole $M_{CO_2}$ = molecular weight of $CO_2$, 44.01 g/mole

Example 4C

Calcimetry (Eijkelkamp, ART No 08.53, Agrisearch Equipment, Morrisville, NC) was also used to determine degree of carbonation (c) volumetrically. The sample was placed in a flask bottle connected to a burette and the beginning water level was recorded. When hydrochloric acid was added to the sample, the carbonates available in the sample convert into $CO_2$ gas leading to rise in water level. Carbonate percentage was computed by measuring the volume of carbon dioxide evolved during the reaction of samples with hydrochloric acid. Degree of carbonation (c) can be calculated from the following equation:

$$n_{re-CaSiO3} = n_{CaCO3} = \frac{m_{CaCO3}}{M_{CaCO3}}$$

$$n_{un-CaSiO3} = \left[\frac{(100 - (n_{CaCO3} * M_{CaCO3}) - (n_{SiO2} \times M_{SiO2}))}{M_{CaSiO3}}\right]$$

$$\lambda_C(\text{mol }\%) = \frac{(n_{re-CaSiO3})}{(n_{un-CaSiO3}) + (n_{re-CaSiO3})} \times 100$$

$n_{re-CaSiO3}$ = mole of reacted $CaSiO3$ $n_{re-CaSiO3}$ = mole of unreacted $CaSiO3$ $n_{CaCO3}$ = mole of $CO_2$ released from the sample $n_{SiO2}$ = mole of $SiO_2$ $M$ = moleculer weight

Example 4D

Relative density ($\rho r$) was calculated from measured bulk density ($\rho b$) with respect to theoretical density ($\rho th$) as follows:

$$\rho_r = \left(\frac{\rho_b}{\rho_{th}}\right)$$

Example 4E

Bulk density was measured by mercury porosimeter (Autopore IV, 9400, Micromeritics Instrument Corp., Nocross, GA). Apparent density ($\rho_a$) of the compacts was measured by helium pycnometer (Accupyc-1430, Micromeritics Instrument Corp., Nocross, GA). Theoretical density ($\rho th$) of composites was calculated from rule of the mixtures, using volume percent (v) of each phase calculated from their degree of carbonation as follows:

$$\rho_{th} = (v_{CaCO3} \times \rho_{CaCO3}) + (v_{CaSiO3} \times \rho_{CaSiO3}) + (v_{SiO2} \times \rho_{SiO2})$$

Where v is volume percent and p is theoretical density of corresponding phase in the composite. Theoretical density of $CaCO_3$ phases formed by carbonation was calculated from Rietveld analysis data using volume percent of each $CaCO_3$ phase and their theoretical densities.

Theoretical density ($\rho th$) (true density) was also directly measured by pycnometer method after the sample was ground until there is no more increase in density with smaller particle size, so closed pores were eliminated.

Example 4F

Porosity and pore size distribution of the ceramic compacts were measured by Mercury (Hg) Intrusion Porosimetry (MIP, AutoPore IV 9400, Micromeritics Instrument Corp., Norcross, GA). Prior the measurement, the samples were oven-dried overnight at 90° C.

Example 4G

The specific surface area of the samples was measured using the Brunauer-Emmett-Teller (BET) method (TriStar II 3020, Micromeritics Corp., Norcross, GA). Prior the measurement, the samples were degassed in a degasser (VacPrep061, Micromeritics Corp., Norcross, GA) under flowing nitrogen gas overnight at 300° C.

Example 4H

Sample microstructure of ion beam milled sections was observed by field emission scanning electron microscopy (FESEM) using a Zeiss Sigma FESEM (Carl Zeiss, Oberkochen, Germany) at an accelerating voltage of 15 kV and working distance of 8.5 m. Sample surfaces were cross-section milled (C5) for 5 h and subsequent flat milled for 5 min at 6 kV accelerating voltage using an ion beam milling system (Hitachi IM4000, Hitachi High-Technologies Corp., Tokyo, Japan). Sample surfaces were sputter coated with 30 nm thick gold coatings (Electron Microscopy Sciences, model EMS 150T ES, PA). Energy Dispersive Spectroscopy (EDS) was also used to measure chemical composition.

Example 5. Mechanical Properties

Compressive strength, three-point flexural strength and fracture toughness of ceramic compacts were measured by a mechanical testing machine (Model 4505, Instron Corp., Canton, MA).

Example 5A

Compressive strength measurements were performed using 100 kN load cell equipped test frame at a crosshead speed of 0.5 mm/min on cylindrical samples with ca. 13 mm in height and ca. 13 mm in diameter. A set of 6 samples was used to calculate mean compressive strength and its standard deviation (shown in parenthesis). The elastic modulus for each sample was determined from the slope of a linear portion of the stress vs strain plot of compressive test data.

Example 5B

Flexural Strength was obtained in a three-point bending with 40 mm span size and using 1 kN load cell equipped test frame, at a crosshead speed of 0.5 mm/min on samples with dimensions of 6 mm×3 mm×45 mm. Flexural strength was calculated using the following equation:

$$\sigma_{3pb} = \frac{3PL}{2BD^2}$$

where P is break force, L is span size, B is width, and D is thickness of a specimen. An average of 6 samples was used to calculate the average strength and its standard deviation (shown in parenthesis).

Example 5C

Hardness was measured by Vickers micro-hardness indentations (VHN, M-400-G3, LECO Corporation, St. Joseph, MI) by applying a load of 9.8 N for 10 seconds on polished samples (ASTM 1327). After indentation, indentation diameters were measured using an optical microscopy (Keyence Corp, VHX-5000, Itasca, IL). Hardness was calculated according to the following equation:

$$H = 0.0018544\left(\frac{P}{d^2}\right)$$

where P is force (N) and d is the average indentation diagonal (mm).

Example 5D

The fracture toughness of ceramic compacts was measured by chevron notch flexure method following the ASTM C-1421 standard. Since both mechanical strength and toughness are the fundamental properties for bone replacement materials, sample sets meet a compressive strength criteria of 130 MPa and flexural strength criteria of 50 MPa or higher were selected for fractural toughness evaluation. Sample dimensions were 6.35 mm×6.35 mm× 45 mm which corresponds to the geometry B in the standard. An average of 8 samples was used for fracture toughness measurements. The notches were cut on using a diamond blade with a thickness of 0.15 mm using a custom designed fixture. Chevron-notched beams were fractured in a three point flexural test fixture (40 mm span) with a crosshead rate of 0.025 mm/min. The chevron notch fracture toughness $(K_{Ivb})$ was calculated using the following equation:

$$K_{Ivb} = Y^*_{min}\left[\frac{P_{max}S_o 10^{-6}}{BW^{3/2}}\right]$$

Where Y*min is the minimum stress intensity factor, Pmax is maximum load (N) that occurs during stable crack propagation; So is the outer support span (mm); B is the specimen width (mm); and W is the specimen thickness (mm). Load-time curves were used to evaluate stable crack growth. Post-test measurements were performed using optical microscopy (Keyence Corp, VHX-5000, Itasca, IL) at 30× magnification. The crack surfaces and microstructure sections perpendicular to crack surface were observed using electron microscopy (FESEM) (Carl Zeiss, Oberkochen, Germany) to define fracture mode and crack propagation paths in these ceramics respectively. Microstructure sections were ground using SiC sandpaper with grit sizes of 600, 800, and 1200. Sample surfaces were sputter coated with 30 nm thick gold coatings (Electron Microscopy Sciences, model EMS 150T ES, Hatfield, PA).

Example 6. In Vitro Evaluation

Example 6A

Ion dissolution and apatite formation on $CaSiO_3$ ceramics in SBF

Specimens 3 mm thick discs were cut from the cylindrical samples using a precision saw (Pace Technologies, Tucson, AZ) for both the SBF ion dissolution studies and the in vitro cell tests. These discs were ultrasonically washed in deionized water, and subsequently dried in air for 12 h at 90° C.

Dissolution behavior and apatite forming ability of $CaSiO_3$ ceramics processed by HTS, LTS, and HLTS were assessed by infiltrating $CaSiO_3$ ceramics in Simulated Body Fluid (SBF). SBF was prepared according to the method reported by Kokubo (Table 3) to possess similar ion concentrations to those found in human blood plasma. The prepara-tion was conducted by dissolving reagent grade $NaCl$, $NaHCO_3$, $KCl$, $K_2HPO_4.3H_2O$, $MgCl_2.6H_2O$, $CaCl_2$), and $Na_2SO_4$ in deionized water, and buffered at pH=7.4 with tris(hydroxymethyl) aminomethane $(CH_2OH)_3CNH_2$ and 1 M HCl at 36.5° C. After ultrasonic washing in deionized water, the discs were sterilized in an autoclave for 20 min. Each sample was then soaked in 50 ml of SBF with a pH comparable to that of human blood plasma and maintained at 36.5° C. for 1, 7, 14, and 21 days. Osteoinductive 45S5 Bioglass® [45% $SiO_2$, 24.5% CaO, 24.5% $Na_2O$ and 6% $P_2O_5$ (wt %)], (MO-SCI Corporation, Rolla, MO) discs were used as a control for comparison.

After soaking in SBF, the samples were rinsed with deionized water, and dried at room temperature. The apatite formation on the specimen surfaces was examined by Thin-Film X-Ray Diffraction (TF-XRD), Field Emission Scanning Electron Microscopy (FE-SEM) and Energy Dispersive Spectroscopy (EDS). Specimens were examined both before and after immersion in SBF using TF-XRD (ADVANCE D8, Bruker-AXS, Madison, WI, USA) at a glancing beam angle of 10 with Cu-Kα X-ray radiation from a source operating at 40 kV and 40 mA. The surface morphologies were observed by FESEM using a Zeiss Sigma FESEM (Carl Zeiss, Oberkochen, Germany) at an accelerating voltage of 15 kV and working distance of 8.5 mm. Sample surfaces were sputter coated with carbon (Electron Microscopy Sciences, model EMS 150T ES, Hatfield, PA). The distribution of elements was analyzed using an EDS detector on the FESEM.

Dissolution behavior of $CaSiO_3$ scaffolds processed by HTS, LTS, and HLTS was evaluated by measuring changes in the ion concentrations of Ca and Si in the SBF solution after immersion using Inductively Coupled Plasma Optical Emission Spectroscopy (ICP-OES; Perkin Elmer, Optima 7300DV, Shelton, CT). The changes in the pH were determined using an electrolyte-type pH meter (HI 2221, Hanna Instruments, Woonsocket, RI). The dissolution of the scaffold material in SBF was followed by concomitant apatite formation as well as weight loss of the scaffolds. Weight loss of samples as a function of time of dissolution in the SBF were calculated from their measured, overnight oven-dried at 90° C., initial weight and final weight after SBF immersion. Sample weights were determined for specimens dried at 90° C. overnight. The weight loss, ICP, and pH values reported are averages of three-fold replication.

Example 6B. Cytotoxicity Assay

To evaluate if possible toxic substances leached from the $CaSiO_3$ samples, cytotoxicity tests were performed that used mouse osteoblast progenitor cells (MC3T3) exposed to the eluents of $CaSiO_3$ scaffolds processed by HTS, LTS and HLTS. $CaSiO_3$ discs were sterilized by autoclaving for 20 min. To prepare the eluents, each disc was placed in a well of a 24-well tissue culture plate (Denville Scientific, Deville, NJ) and 1 ml of alpha-MEM complete medium (alpha-MEM medium+10% fetal bovine serum) (Gibco, Grand Island, NY) was added to each disc. After incubation at 37° C. for 24 h, the medium (eluent) from each disc was collected and transferred to a corresponding well of new 24-well plate. Mouse osteoblast progenitor cells MC3T3 (P2-P4) (ATCC, Manassas, VA) cultured in 10 cm tissue culture dish (Denville Scientific, Deville, NJ) were trypsinized by adding 1 ml of 0.25% trypsin-EDTA (Gibco, Grand Island, NY) and incubated for 5 min. Cells were resuspended in alpha-MEM complete medium at $5\times10^5$/ml. The cells of 0.2 ml were added to the wells containing eluent or alpha-MEM complete medium (control) and the plates were incubated at 37° C. with 5% $CO_2$ and >95% humidity for 24 h.

Afterwards, the eluent was removed and each well was washed with Phosphate Buffered Saline (PBS) (Gibco, Grand Island, NY) twice. The cell viability was measured using alamarBlue assay, which measures the natural reducing power of living cells to convert resazurin to the fluorescent molecule, resorufin (BUF012B AbD Serotec). 300 µl of medium containing 10% alamar Blue was added to each well, after incubation for 1 h at 37° C., 100 µl of medium from each well was transferred to a 96-well plate (Denville Scientific, Deville, NJ). The fluorescence intensity at 590 nm of resorufinat excited at 560 nm was read using a TeCan fluorometer (Infinite M200, Mannedorf, Switzerland). The relative viability of cells in each eluent was normalized to the viability of cells cultured in alpha-MEM complete medium.

Example 6C

Cell Adhesion and Proliferation on Discs MC3T3 cells adhesion to the composite discs was evaluated as follows: Sterilized discs were washed with Phosphate Buffered Saline (PBS) three times. Composite discs were placed in the wells of a 24-well plate and 1 ml of MC3T3 cells were seeded onto each disc or Tissue Culture Polystyrene Surface (TCPS) at $2.5\times10^4$/well in alpha-MEM complete medium. After incubation for 24 h, the discs were transferred to a new wells and the cells were washed with PBS twice. 500 µl of medium containing 10% alamarBlue was added to each well and incubated at 37° C. for 1 h. 100 µl of medium from each well was transferred to a 96-well plate and the fluorescence intensity at 590 nm of resorufinat excited at 560 nm was measured using a TeCan fluorometer (M200). The cell adhesion on each disc at 24 h was calculated as the relative viability of cells on disc normalized to the viability of cells on TCPS.

To monitor cell proliferation, after the alamarBlue assay, cells on composite discs or TCPS were washed with PBS twice and recovered in complete medium for 2 h. Once the medium was removed, 1 ml of fresh medium was added to the cells. Cell proliferation was evaluated after incubation for 1, 7, 14 and 20 days by measurement of the cell viability using alamarBlue assay. The relative viability of cells on discs or TCPS at each time point was normalized to its own viability at day 1.

Example 6D. Cell Differentiation on Discs

In vitro osteoinductivity of a material is measured by the material's ability to induce osteogenic differentiation, or to differentiate stem cells to osteoblasts. The ability of HTS, LTS, and HLTS processed $CaSiO_3$ scaffolds to induce cell differentiation was evaluated. Samples of 12 mm in diameter and 3 mm in thickness were prepared.

Osteoinductive 45S5 Bioglass® [45% $SiO_2$, 24.5% CaO, 24.5% $Na_2O$ and 6% $P_2O_5$ (Wt %)], (MO-SCI Corporation, Rolla, MO) discs with 12 mm in diameter and 1 mm in thickness were used as a control for comparison of osteogenicity. Sterilized discs were placed in the wells of a 24-well non-treated tissue culture plate. 1 mL of human mesenchymal stem cells (hMSCs, Lonza, passage <6) were seeded onto each disc at $2.5\times10^4$ cells/well in complete alpha-MEM medium (alpha-MEM medium+10% fetal bovine serum). Samples were incubated for 24 h. After 24 h, the discs were transferred to a fresh plate. Cells were cultured for 14 days, with media changes every 2-3 days.

On day 14, alkaline phosphatase (ALP) activity was quantified using an Alkaline Phosphatase Activity Fluorometric Assay Kit (Biovision, Milpitas, CA) according to manufacturer's instructions. Briefly, enzymatic activity in the cell lysates was measured by the cleavage of a phosphate group of a non-fluorescent substrate, 4-methylumbelliferyl phosphate disodium salt (MUP), by ALP, which results in a fluorescent signal. The intensity of the fluorescent signal can be used to measure ALP activity using a standard curve. ALP activity was normalized to dsDNA content, which was measured using the Quant-iT Picogreen dsDNA Assay Kit (ThermoFisher, Waltham, MA). This assay uses a fluorescent dye that specifically binds to double stranded DNA.

Example 6E. Statistical Analysis

Data is represented as the mean±standard error of the mean. Statistical analysis was performed in Prism 7.0 (Graphpad Software, La Jolla, CA) using one-way ANOVA with post-hoc Tukey's test. $p<0.05$ was considered statistically significant.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A composite material comprising:

a porous, carbonated, calcium silicate ceramic having a microstructure comprising interconnected open pores;

wherein the calcium silicate surface defining said pores is partially or completely coated with an amorphous silica layer, and said silica coating comprises an overlayer of calcium carbonate crystals;

wherein said silica coating and said calcium carbonate overlayer form a network that interconnects throughout said ceramic microstructure, but does not completely occlude said pores; and wherein the composite material is in the form of a scaffold for implantation in vivo.

2. The composite material of claim 1, produced by:

i) providing a $CaSiO_3$ ceramic compact having a microstructure comprising interconnected open pores around ceramic grain boundaries; and ii) subjecting said compact to hydrothermal carbonation under Low Temperature Solidification (LTS) conditions comprising heating in about 10 to about 30 psig $CO_2$ gas at <100° C., until the relative density increases by about 16% to about 20%.

3. The composite material of claim 2, wherein said $CaSiO_3$ ceramic compact is sintered at a temperature between about 1100° C. and about 1200° C. and cooled before subjecting to LTS conditions.

4. The composite material of claim 3, wherein said $CaSiO_3$ ceramic compact is sintered at about 1150° C.

5. The composite material of claim 2, wherein said LTS conditions comprise heating at a temperature of about 50° C. to <100° C. in about 15 to about 25 psig $CO_2$ gas.

6. The composite material of claim 5, wherein said LTS conditions comprise heating at about 90° C. in about 20 psig $CO_2$ gas.

7. The composite material of claim 2, wherein said compact has a shape with dimensions to fit a bone defect prior to or after sintering.

8. A method of repairing a bone defect caused by trauma, infection or removal of a tumor, said method comprising filling said defect with the composite material of claim 1.

9. A method for enhancing osteoblast proliferation comprising exposing osteoblasts to an effective amount of the calcium silicate composite of claim 1, or its aqueous extract.

10. A method for stimulating osteogenic cell differentiation comprising exposing human mesenchymal stem cells (hMSCs) to an effective amount of the calcium silicate composite of claim 1, or its aqueous extract, thereby upregulating one or more osteogenic markers involved in osteogenic differentiation, osteogenic function or a combination thereof.

11. A composite material comprising:

a porous, carbonated, calcium silicate ceramic having a microstructure comprising interconnected open pores;

wherein the calcium silicate surface defining said pores is partially or completely coated with an amorphous silica layer, and said silica coating comprises an overlayer of calcium carbonate crystals;

wherein said silica coating and said calcium carbonate overlayer form a network that interconnects throughout said ceramic microstructure, but does not completely occlude said pores; and wherein the amorphous silica layer comprises a calcium gradient.

12. The composite material of claim 11, produced by:

i) providing a $CaSiO_3$ ceramic compact having a microstructure comprising interconnected open pores around ceramic grain boundaries; and ii) subjecting said compact to hydrothermal carbonation under Low Temperature Solidification (LTS) conditions comprising heating in about 10 to about 30 psig $CO_2$ gas at <100° C., until the relative density increases by about 16% to about 20%.

13. The composite material of claim 12, wherein said $CaSiO_3$ ceramic compact is sintered at a temperature between about 1100° C. and about 1200° C. and cooled before subjecting to LTS conditions.

14. The composite material of claim 13, wherein said $CaSiO_3$ ceramic compact is sintered at about 1150° C.

15. The composite material of claim 12, wherein said LTS conditions comprise heating at a temperature of about 50° C. to <100° C. in about 15 to about 25 psig $CO_2$ gas.

16. The composite material of claim 15, wherein said LTS conditions comprise heating at about 90° C. in about 20 psig $CO_2$ gas.

17. The composite material of claim 12, wherein said compact has a shape with dimensions to fit a bone defect prior to or after sintering.

18. A method of repairing a bone defect caused by trauma, infection or removal of a tumor, said method comprising filling said defect with the composite material of claim 11.

19. A method for enhancing osteoblast proliferation comprising exposing osteoblasts to an effective amount of the calcium silicate composite of claim 11, or its aqueous extract.

* * * * *